(12) United States Patent
Robinson

(10) Patent No.: US 9,259,218 B2
(45) Date of Patent: Feb. 16, 2016

(54) TISSUE ANCHOR AND ANCHORING SYSTEM

(71) Applicant: Mitralign, Inc., Tewksbury, MA (US)

(72) Inventor: Jason Robinson, Windham, NH (US)

(73) Assignee: MITRALIGN, INC., Tewksbury, MA (US)

( * ) Notice: Subject to any disclaimer, the term of this patent is extended or adjusted under 35 U.S.C. 154(b) by 358 days.

(21) Appl. No.: 13/777,042

(22) Filed: Feb. 26, 2013

(65) Prior Publication Data

US 2014/0243859 A1  Aug. 28, 2014

(51) Int. Cl.
  *A61B 17/04* (2006.01)
  *A61B 17/00* (2006.01)

(52) U.S. Cl.
  CPC ... *A61B 17/0401* (2013.01); *A61B 2017/00243* (2013.01); *A61B 2017/00783* (2013.01); *A61B 2017/0406* (2013.01); *A61B 2017/0419* (2013.01); *A61B 2017/0464* (2013.01)

(58) Field of Classification Search
  CPC ........... A61B 17/0057; A61B 17/0401; A61B 17/0404; A61B 17/0406; A61B 17/0469; A61B 2017/0419; A61B 2017/0464; A61B 2017/0475; A61B 2017/048; A61B 2017/0496
  See application file for complete search history.

(56) References Cited

U.S. PATENT DOCUMENTS

| 2,143,910 A | 1/1939 | Didusch |
| 3,674,014 A | 7/1972 | Tillander |
| 3,794,041 A | 2/1974 | Frei et al. |
| 3,841,521 A | 10/1974 | Jarvik |
| 3,959,960 A | 6/1976 | Santos |
| 3,986,493 A | 10/1976 | Hendren, III |

(Continued)

FOREIGN PATENT DOCUMENTS

| CN | 101252887 | 8/2008 |
| CN | 102525583 | 7/2012 |

(Continued)

OTHER PUBLICATIONS

Cardiac Surgery Renaissance, Anatomical Landscape; Composite Profile of CABG and Valve Procedures, Apr. 25, 1996, Cardiology Roundtable Interviews.

(Continued)

*Primary Examiner* — Eric Rosen
*Assistant Examiner* — Todd J Scherbel
(74) *Attorney, Agent, or Firm* — Leason Ellis LLP

(57) ABSTRACT

A tissue anchor includes a generally flexible elongate continuous anchor member capable of being inserted through tissue and moving between an elongate configuration and a shortened configuration suitable for anchoring against at least one side of the tissue. The anchor member has a first set of openings and a second set of openings formed therein at spaced locations along a length of the anchor member. The tissue anchor also includes a tensioning member operatively connected to the anchor member and the tensioning member extends through the proximal end portion to the distal end portion by passing through the first set of openings and then back to the proximal end portion by passing through the second set of openings. The anchor member is configured to form a plurality of folded panels upon pulling the tensioning member. The plurality of folded panels comprises a set of first panels that are oriented in a first direction and at least one second panel that is oriented in a second direction that is perpendicular to the folded set of first panels.

15 Claims, 26 Drawing Sheets

(56) References Cited

U.S. PATENT DOCUMENTS

| | | |
|---|---|---|
| 3,995,619 A | 12/1976 | Glatzer |
| 4,042,979 A | 8/1977 | Angell |
| 4,055,861 A | 11/1977 | Carpentier et al. |
| 4,258,705 A | 3/1981 | Sorensen et al. |
| 4,369,787 A | 1/1983 | Lasner et al. |
| 4,489,446 A | 12/1984 | Reed |
| 4,532,926 A | 8/1985 | O'Holia |
| 4,809,713 A | 3/1989 | Grayzel |
| 4,917,698 A | 4/1990 | Carpentier et al. |
| 4,945,912 A | 8/1990 | Langberg |
| 5,016,353 A | 5/1991 | Iten |
| 5,041,129 A | 8/1991 | Hayhurst et al. |
| 5,041,130 A | 8/1991 | Cosgrove et al. |
| 5,061,277 A | 10/1991 | Carpentier et al. |
| 5,104,407 A | 4/1992 | Lam et al. |
| 5,123,914 A | 6/1992 | Cope |
| 5,171,232 A | 12/1992 | Castillo et al. |
| 5,171,259 A | 12/1992 | Inoue |
| 5,192,302 A | 3/1993 | Kensey et al. |
| 5,201,880 A | 4/1993 | Wright et al. |
| 5,203,777 A | 4/1993 | Lee |
| 5,304,190 A | 4/1994 | Reckelhoff et al. |
| 5,306,234 A | 4/1994 | Johnson |
| 5,306,296 A | 4/1994 | Wright et al. |
| 5,337,736 A | 8/1994 | Reddy |
| 5,360,444 A | 11/1994 | Kusuhara |
| 5,364,365 A | 11/1994 | Wortrich |
| 5,364,393 A | 11/1994 | Auth et al. |
| 5,429,131 A | 7/1995 | Scheinman et al. |
| 5,450,860 A | 9/1995 | O'Connor |
| 5,452,513 A | 9/1995 | Zinnbauer et al. |
| 5,464,023 A | 11/1995 | Viera |
| 5,545,178 A | 8/1996 | Kensey et al. |
| 5,565,122 A | 10/1996 | Zinnbauer et al. |
| 5,571,215 A | 11/1996 | Sterman et al. |
| 5,593,424 A | 1/1997 | Northrup |
| 5,607,471 A | 3/1997 | Seguin et al. |
| 5,623,943 A | 4/1997 | Hackett et al. |
| 5,626,590 A | 5/1997 | Wilk |
| 5,640,955 A | 6/1997 | Ockuly et al. |
| 5,669,919 A | 9/1997 | Sanders et al. |
| 5,674,279 A | 10/1997 | Wright et al. |
| 5,682,906 A | 11/1997 | Sterman et al. |
| 5,690,656 A | 11/1997 | Cope et al. |
| 5,706,827 A | 1/1998 | Ehr et al. |
| 5,716,367 A | 2/1998 | Koike et al. |
| 5,716,397 A | 2/1998 | Myers |
| 5,716,399 A | 2/1998 | Love |
| 5,776,080 A | 7/1998 | Thome et al. |
| 5,776,189 A | 7/1998 | Khalid |
| 5,797,939 A | 8/1998 | Yoon |
| 5,813,996 A | 9/1998 | St. Germain et al. |
| 5,824,066 A | 10/1998 | Gross |
| 5,827,300 A | 10/1998 | Fleega |
| 5,829,447 A | 11/1998 | Stevens et al. |
| 5,830,224 A | 11/1998 | Cohn et al. |
| 5,851,185 A | 12/1998 | Berns |
| 5,860,920 A | 1/1999 | McGee et al. |
| 5,868,733 A | 2/1999 | Ockuly et al. |
| 5,879,366 A | 3/1999 | Shaw |
| 5,888,240 A | 3/1999 | Carpentier et al. |
| 5,906,579 A | 5/1999 | Vander Salm et al. |
| 5,911,720 A | 6/1999 | Bourne et al. |
| 5,928,224 A | 7/1999 | Laufer |
| 5,931,818 A | 8/1999 | Werp et al. |
| 5,944,738 A | 8/1999 | Amplatz et al. |
| 5,980,515 A | 11/1999 | Tu |
| 5,984,939 A | 11/1999 | Yoon |
| 6,015,414 A | 1/2000 | Werp et al. |
| 6,027,514 A | 2/2000 | Stine et al. |
| 6,042,581 A | 3/2000 | Ryan et al. |
| 6,050,472 A | 4/2000 | Shibata |
| 6,050,936 A | 4/2000 | Schweich, Jr. et al. |
| 6,068,637 A | 5/2000 | Popov et al. |
| 6,068,648 A | 5/2000 | Cole et al. |
| 6,071,292 A | 6/2000 | Makower et al. |
| 6,080,182 A | 6/2000 | Shaw et al. |
| 6,099,460 A | 8/2000 | Denker |
| 6,102,945 A | 8/2000 | Campbell |
| 6,113,611 A | 9/2000 | Allen et al. |
| 6,126,647 A | 10/2000 | Posey et al. |
| RE36,974 E | 11/2000 | Bonutti |
| 6,159,234 A | 12/2000 | Bonutti |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,183 A | 12/2000 | Kuehn et al. |
| 6,173,199 B1 | 1/2001 | Gabriel |
| 6,190,353 B1 | 2/2001 | Makower et al. |
| 6,197,017 B1 | 3/2001 | Brock et al. |
| 6,206,895 B1 | 3/2001 | Levinson |
| 6,210,432 B1 | 4/2001 | Solem et al. |
| 6,231,587 B1 | 5/2001 | Makower |
| 6,267,781 B1 | 7/2001 | Tu |
| 6,269,819 B1 | 8/2001 | Oz et al. |
| 6,285,903 B1 | 9/2001 | Rosenthal et al. |
| 6,287,317 B1 | 9/2001 | Makower et al. |
| 6,298,257 B1 | 10/2001 | Hall et al. |
| 6,306,133 B1 | 10/2001 | Tu et al. |
| 6,312,447 B1 | 11/2001 | Grimes |
| 6,319,263 B1 | 11/2001 | Levinson |
| 6,332,089 B1 | 12/2001 | Acker et al. |
| 6,332,893 B1 | 12/2001 | Mortier et al. |
| 6,352,543 B1 | 3/2002 | Cole |
| 6,385,472 B1 | 5/2002 | Hall et al. |
| 6,401,720 B1 | 6/2002 | Stevens et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,447,522 B2 | 9/2002 | Gambale et al. |
| 6,461,366 B1 | 10/2002 | Seguin |
| 6,500,184 B1 | 12/2002 | Chan et al. |
| 6,524,303 B1 | 2/2003 | Garibaldi |
| 6,530,952 B2 | 3/2003 | Vesely |
| 6,537,198 B1 | 3/2003 | Vidlund et al. |
| 6,537,314 B2 | 3/2003 | Langberg et al. |
| 6,542,766 B2 | 4/2003 | Hall et al. |
| 6,544,230 B1 | 4/2003 | Flaherty et al. |
| 6,554,852 B1 | 4/2003 | Oberlander |
| 6,562,019 B1 | 5/2003 | Sell |
| 6,565,562 B1 | 5/2003 | Shah et al. |
| 6,589,208 B2 | 7/2003 | Ewers et al. |
| 6,594,517 B1 | 7/2003 | Nevo |
| 6,596,014 B2 | 7/2003 | Levinson et al. |
| 6,619,291 B2 | 9/2003 | Hlavka et al. |
| 6,626,899 B2 | 9/2003 | Houser et al. |
| 6,626,919 B1 | 9/2003 | Swanstrom |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,655,386 B1 | 12/2003 | Makower et al. |
| 6,656,221 B2 | 12/2003 | Taylor et al. |
| 6,669,687 B1 | 12/2003 | Saadat |
| 6,669,707 B1 | 12/2003 | Swanstrom et al. |
| 6,676,702 B2 | 1/2004 | Mathis |
| 6,689,164 B1 | 2/2004 | Seguin |
| 6,699,263 B2 | 3/2004 | Cope |
| 6,702,825 B2 | 3/2004 | Frazier et al. |
| 6,702,826 B2 | 3/2004 | Liddicoat et al. |
| 6,718,985 B2 | 4/2004 | Hlavka et al. |
| 6,723,038 B1 | 4/2004 | Schroeder et al. |
| 6,730,112 B2 | 5/2004 | Levinson |
| 6,733,509 B2 | 5/2004 | Nobles et al. |
| 6,736,808 B1 | 5/2004 | Motamedi et al. |
| 6,746,472 B2 | 6/2004 | Frazier et al. |
| 6,764,500 B1 | 7/2004 | Muijs Van De Moer et al. |
| 6,769,434 B2 | 8/2004 | Liddicoat et al. |
| 6,793,618 B2 | 9/2004 | Schweich, Jr. et al. |
| 6,866,673 B2 | 3/2005 | Oren et al. |
| 6,913,608 B2 | 7/2005 | Liddicoat et al. |
| 6,921,407 B2 | 7/2005 | Nguyen et al. |
| 6,923,823 B1 | 8/2005 | Bartlett et al. |
| 6,942,694 B2 | 9/2005 | Liddicoat et al. |
| 6,945,978 B1 | 9/2005 | Hyde |

(56) References Cited

U.S. PATENT DOCUMENTS

| | | |
|---|---|---|
| 6,964,683 B2 | 11/2005 | Kowalsky et al. |
| 6,976,995 B2 | 12/2005 | Mathis et al. |
| 7,004,958 B2 | 2/2006 | Adams et al. |
| 7,037,334 B1 | 5/2006 | Hlavka et al. |
| 7,101,395 B2 | 9/2006 | Tremulis et al. |
| 7,115,110 B2 | 10/2006 | Frazier et al. |
| 7,166,127 B2 | 1/2007 | Spence et al. |
| 7,211,094 B2 | 5/2007 | Gannoe et al. |
| 7,247,134 B2 | 7/2007 | Vidlund et al. |
| 7,731,732 B2 | 6/2010 | Ken |
| 7,749,250 B2 | 7/2010 | Stone et al. |
| 7,771,455 B2 | 8/2010 | Ken |
| 7,883,538 B2 | 2/2011 | To et al. |
| 7,931,580 B2 | 4/2011 | Gertner et al. |
| 8,172,871 B2 | 5/2012 | Ken |
| 8,932,325 B2 * | 1/2015 | Stanley et al. ............ 606/213 |
| 2001/0005787 A1 | 6/2001 | Oz et al. |
| 2001/0039436 A1 | 11/2001 | Frazier et al. |
| 2001/0049492 A1 | 12/2001 | Frazier et al. |
| 2002/0013571 A1 | 1/2002 | Goldfarb et al. |
| 2002/0016628 A1 | 2/2002 | Langberg et al. |
| 2002/0019649 A1 | 2/2002 | Sikora et al. |
| 2002/0026198 A1 | 2/2002 | Ockuly et al. |
| 2002/0026216 A1 | 2/2002 | Grimes |
| 2002/0029080 A1 | 3/2002 | Mortier et al. |
| 2002/0042621 A1 | 4/2002 | Liddicoat et al. |
| 2002/0072758 A1 | 6/2002 | Reo et al. |
| 2002/0087169 A1 | 7/2002 | Brock et al. |
| 2002/0087173 A1 | 7/2002 | Alferness et al. |
| 2002/0087178 A1 | 7/2002 | Nobles et al. |
| 2002/0095167 A1 | 7/2002 | Liddicoat et al. |
| 2002/0100485 A1 | 8/2002 | Stevens et al. |
| 2002/0103532 A1 | 8/2002 | Langberg et al. |
| 2002/0107531 A1 | 8/2002 | Schreck et al. |
| 2002/0128708 A1 | 9/2002 | Northrup, III et al. |
| 2002/0156526 A1 | 10/2002 | Hlavka et al. |
| 2002/0165535 A1 | 11/2002 | Lesh et al. |
| 2002/0169359 A1 | 11/2002 | McCarthy et al. |
| 2002/0169502 A1 | 11/2002 | Mathis |
| 2002/0169504 A1 | 11/2002 | Alferness et al. |
| 2002/0173841 A1 | 11/2002 | Ortiz et al. |
| 2002/0183766 A1 | 12/2002 | Seguin |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0078671 A1 | 4/2003 | Lesniak et al. |
| 2003/0083538 A1 | 5/2003 | Adams et al. |
| 2003/0105474 A1 | 6/2003 | Bonutti |
| 2003/0105520 A1 | 6/2003 | Alferness et al. |
| 2003/0120340 A1 | 6/2003 | Liska et al. |
| 2003/0130730 A1 | 7/2003 | Cohn et al. |
| 2003/0144697 A1 | 7/2003 | Mathis et al. |
| 2003/0160721 A1 | 8/2003 | Gilboa et al. |
| 2003/0171776 A1 | 9/2003 | Adams et al. |
| 2003/0171806 A1 | 9/2003 | Mathis et al. |
| 2003/0199974 A1 | 10/2003 | Lee et al. |
| 2003/0204205 A1 | 10/2003 | Sauer et al. |
| 2003/0208195 A1 | 11/2003 | Thompson et al. |
| 2003/0212453 A1 | 11/2003 | Mathis et al. |
| 2003/0220685 A1 | 11/2003 | Hlavka et al. |
| 2003/0233142 A1 | 12/2003 | Morales et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0044364 A1 | 3/2004 | DeVries et al. |
| 2004/0049211 A1 | 3/2004 | Tremulis et al. |
| 2004/0092962 A1 | 5/2004 | Thornton et al. |
| 2004/0093023 A1 | 5/2004 | Allen et al. |
| 2004/0097865 A1 | 5/2004 | Anderson et al. |
| 2004/0122456 A1 | 6/2004 | Saadat et al. |
| 2004/0127983 A1 | 7/2004 | Mortier et al. |
| 2004/0133063 A1 | 7/2004 | McCarthy et al. |
| 2004/0147958 A1 | 7/2004 | Lam et al. |
| 2004/0152947 A1 | 8/2004 | Schroeder et al. |
| 2004/0162568 A1 | 8/2004 | Saadat et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0220473 A1 | 11/2004 | Lualdi |
| 2004/0236419 A1 | 11/2004 | Milo |
| 2004/0243153 A1 | 12/2004 | Liddicoat et al. |
| 2004/0243227 A1 | 12/2004 | Starksen et al. |
| 2004/0260317 A1 | 12/2004 | Bloom et al. |
| 2005/0033446 A1 | 2/2005 | Deem et al. |
| 2005/0049634 A1 | 3/2005 | Chopra |
| 2005/0049681 A1 | 3/2005 | Greenhalgh et al. |
| 2005/0055087 A1 | 3/2005 | Starksen |
| 2005/0055089 A1 | 3/2005 | Macoviak et al. |
| 2005/0065550 A1 | 3/2005 | Starksen et al. |
| 2005/0065601 A1 | 3/2005 | Lee et al. |
| 2005/0075723 A1 | 4/2005 | Schroeder et al. |
| 2005/0107810 A1 | 5/2005 | Morales et al. |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0192599 A1 | 9/2005 | Demarais |
| 2005/0197693 A1 | 9/2005 | Pai et al. |
| 2005/0216039 A1 | 9/2005 | Lederman |
| 2005/0234481 A1 | 10/2005 | Waller |
| 2005/0251157 A1 | 11/2005 | Saadat et al. |
| 2005/0251159 A1 | 11/2005 | Ewers et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267533 A1 | 12/2005 | Gertner |
| 2005/0267571 A1 | 12/2005 | Spence et al. |
| 2005/0283192 A1 | 12/2005 | Torrie et al. |
| 2005/0288694 A1 | 12/2005 | Solomon |
| 2006/0004410 A1 | 1/2006 | Nobis et al. |
| 2006/0009784 A1 | 1/2006 | Behl et al. |
| 2006/0069429 A1 | 3/2006 | Spence et al. |
| 2006/0089525 A1 | 4/2006 | Mamo et al. |
| 2006/0142756 A1 | 6/2006 | Davies et al. |
| 2006/0161040 A1 | 7/2006 | McCarthy et al. |
| 2006/0178682 A1 | 8/2006 | Boehlke |
| 2006/0212045 A1 | 9/2006 | Schilling et al. |
| 2007/0010857 A1 | 1/2007 | Sugimoto et al. |
| 2007/0055303 A1 | 3/2007 | Vidlund et al. |
| 2007/0080188 A1 | 4/2007 | Spence et al. |
| 2007/0106310 A1 | 5/2007 | Goldin et al. |
| 2007/0112424 A1 | 5/2007 | Spence et al. |
| 2008/0228165 A1 | 9/2008 | Spence et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |

(56) References Cited

U.S. PATENT DOCUMENTS

| | | |
|---|---|---|
| 2008/0275503 A1 | 11/2008 | Spence et al. |
| 2009/0018655 A1 | 1/2009 | Brunelle et al. |
| 2012/0116447 A1 | 5/2012 | Stanley et al. |

FOREIGN PATENT DOCUMENTS

| | | |
|---|---|---|
| EP | 1016377 | 7/2000 |
| EP | 2181670 | 5/2010 |
| WO | WO 9604852 | 2/1996 |
| WO | WO 9900059 | 1/1999 |
| WO | WO 0003759 | 1/2000 |
| WO | WO 0044311 | 8/2000 |
| WO | WO 0060995 | 10/2000 |
| WO | WO 0067640 | 11/2000 |
| WO | WO 0200099 | 1/2002 |
| WO | WO 02051329 | 7/2002 |
| WO | WO 02096275 | 12/2002 |
| WO | WO 03001893 | 1/2003 |
| WO | WO 03007796 | 1/2003 |
| WO | WO 03053289 | 7/2003 |
| WO | WO 2004/037317 | 5/2004 |
| WO | WO 2004045378 | 6/2004 |
| WO | WO 2004/112658 | 12/2004 |
| WO | WO 2005011463 | 2/2005 |
| WO | WO 2005013832 | 2/2005 |
| WO | WO 2005025644 | 3/2005 |
| WO | WO 200558239 | 6/2005 |
| WO | WO 2006064490 | 6/2006 |
| WO | WO 2006105008 | 10/2006 |
| WO | WO 2007005394 | 1/2007 |
| WO | WO 200891391 | 7/2008 |
| WO | WO 2012/177305 | 12/2012 |

OTHER PUBLICATIONS

F. Maisano et al., The Double-Orifice Technique as a Standardized Approach to Treat Mitral Regurgitation Due to Severe Myxomatous Disease: Surgical Technique, European Journal of Cardio-thoracis Surgery, 1998.

Douglas P. Zipes, MD et al., Ablation of Free Wall Accessory Pathways, Catheter Ablation of Arrhythmias, Chapter 8, 7 pgs., May 22, 2001.

David L.S. Morales et al., Development of an Off Bypass Mitral Valve Repair, Department of Surgery, Columbia University, College of Physicians and Surgeons, New York, NY. Apr. 13, 1999.

Heart Surgery Forum, Aug. 8, 2000. p. 1. Tables 1-2.Web. <<http://www.hsforum.com/vol2/issue2/1999-4963 tables.html>>.

Heart Surgery Forum, Aug. 8, 2000. pp. 1-4. Figures 1-8.Web. <<http://www.hsforum.comlvol2/issue2/1999-4963figures.html>>.

"Heart Valves: The Duran Flexible Annuloplasty Band—For Surgeons "Partial" to Flexiblity." Medtronic. Feb. 23, 2001. Web. <<http://medtronic.com/cardiac/heartvalves/duran_band/>>.

Zsolt L. Nagy et al., Mitral Annuloplasty With a Suture Technique, European Journal of Cardio-thoracic Surgery 18. Aug. 15, 2000, 1 pg.

* cited by examiner

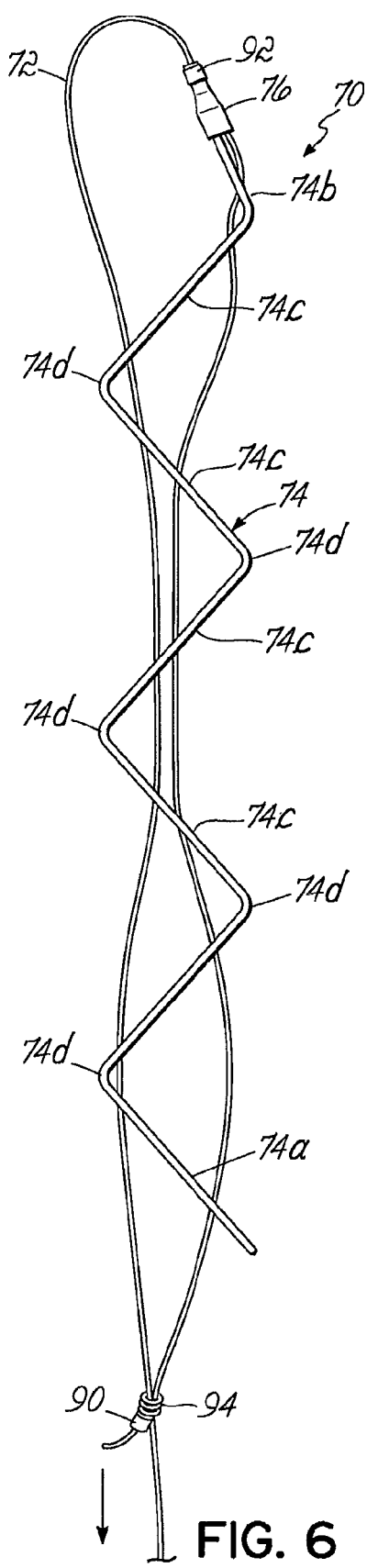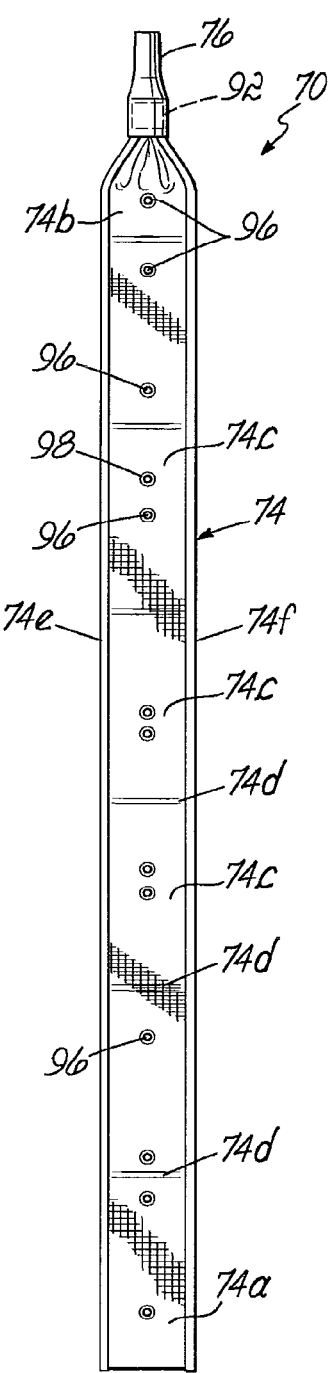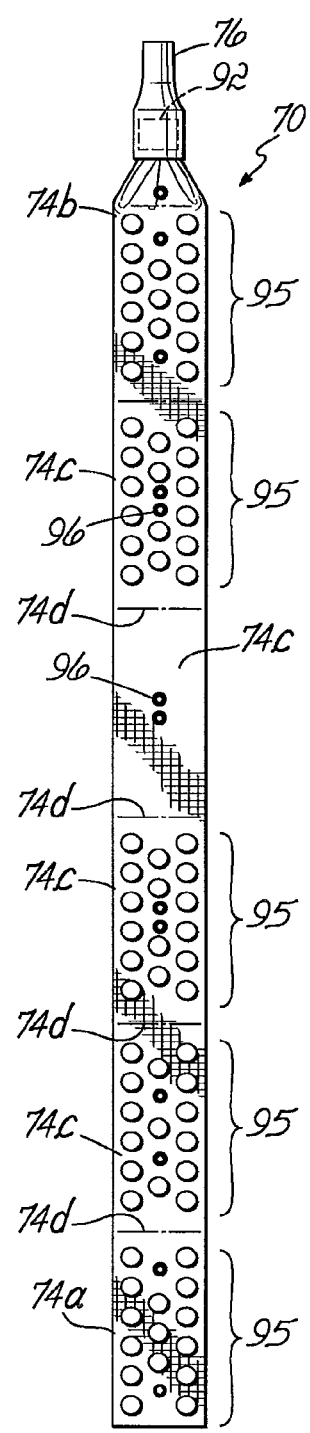
FIG. 6
FIG. 7
FIG. 7A

TISSUE ANCHOR AND ANCHORING SYSTEM

CROSS REFERENCE TO RELATED APPLICATIONS

This application is related to U.S. patent application Ser. No. 12/273,670, filed on Nov. 19, 2008, entitled TISSUE ANCHOR AND ANCHORING SYSTEM, which is a divisional of copending U.S. patent application Ser. No. 11/174,951, filed on Jul. 5, 2005, entitled TISSUE ANCHOR, ANCHORING SYSTEM AND METHODS OF USING THE SAME, each of which is hereby incorporated by reference in its entirety.

TECHNICAL FIELD

The present invention generally relates to tissue anchors and, more particularly, anchors and methods of using such anchors to secure an element or otherwise provide an anchor point to biological tissue and/or to secure at least two tissue portions together.

BACKGROUND

Many different surgical procedures require that an anchor be used to either establish a strong point of connection for other securing elements or devices relative to a tissue location in a patient, and/or to secure two or more tissue layers (i.e., portions together. In this regard, the term "anchor", as used herein, is not to be limited to any particular type of tissue fastening or securement application but, rather, encompasses any hard and/or soft tissue-to-tissue securement, tissue-to-device securement, or any other tissue securement application.

One particular area that has received attention in recent years is that of catheter-based surgical procedures. Various tissue anchors have been developed for purposes of deployment and securement with catheter-based technology. However, there are still limitations in current technology. For example, insertion size versus deployment size must be strictly controlled due to the need for catheter diameters to be maintained relatively small. Many catheter-based tissue anchor systems have very specialized uses and are not versatile for use in many different tissue fastening or securement operations.

There is generally a need for a simpler, more versatile tissue anchor which may be deployed and securely fastened to tissue in a catheter-based operation or a non-catheter-based operation.

SUMMARY

According to one embodiment, a tissue anchor includes a generally flexible elongate continuous anchor member capable of being inserted through tissue and moving between an elongate configuration and a shortened configuration suitable for anchoring against at least one side of the tissue. The anchor member has a proximal end portion, a distal end portion, wherein the anchor member has a first set of openings and a second set of openings formed therein at spaced locations along a length of the anchor member.

The tissue anchor also includes a tensioning member operatively connected to the anchor member such that the anchor member can slide relative to the tensioning member. The tensioning member extends through the proximal end portion to the distal end portion by passing through the first set of openings and then back to an anchor point at the proximal end portion by passing through the second set of openings. The tensioning member is capable of being pulled to cause the anchor member to move relative to the tensioning member from the elongate configuration to the shortened configuration. The anchor member can compress along a length thereof and thereby adjust to a thickness of the tissue between the proximal and distal end portions.

The anchor member is configured to form a plurality of folded panels upon pulling the tensioning member. The plurality of folded panels comprises a set of first panels that are oriented in a first direction and at least one second panel that is oriented in a second direction that is perpendicular to the folded set of first panels.

The first panels can be located in the proximal end portion and at least partially within the distal end portion and the at least one second panel is located within the distal end portion. In addition, the anchor member includes at least one first transitional fold line formed within the distal end portion and a plurality of second fold lines formed both within the proximal and distal end portions. The second fold lines have a different orientation than the first fold line to cause the anchor member to have a change in a folding direction along the distal end portion and relative to folding of an adjacent section of the distal end portion and the proximal end portion upon pulling the tensioning member.

In another embodiment of the present invention, at least some openings belonging to the sets of first and second openings define first pairs of openings each pair defined by one first opening and one second opening. Each first pair of openings is defined by a line that passes through the one first opening and the one second opening, wherein the lines of the associated first pairs of openings are parallel to one another and are perpendicular to a longitudinal axis of the anchor member. The first pairs of openings can be located both within the distal end portion and the proximal end portion. In addition, the first and second sets of openings can share at least one common opening to allow the tensioning member to pass through the shared common opening as the tensioning member travels both toward the distal end portion from the proximal end portion and returns from the distal end portion to the anchor point.

In yet another embodiment, the openings in the first set of openings define a first curve with the openings of the first set in a middle portion of the anchor member being closest to a lateral center of the anchor member and the openings in the second set of openings define a second curve with the openings of the second set in the middle portion being closest to the lateral center. The first and second curves have a lateral distance from each other along a length of the anchor member to thereby define an hour glass shaped pattern.

BRIEF DESCRIPTION OF THE DRAWINGS

FIG. 6 is a side elevation view illustrating the tissue anchor constructed in accordance with the second embodiment;

FIG. 7 is a front view of the elongate strip portion of the anchor;

FIG. 7A is a front elevation view similar to FIG. 7, but illustrating one embodiment of radiopaque markers used on the elongate strip;

FIG. 12b is a side elevation view of the tissue anchor of FIG. 12a;

FIG. 13b is a side elevation view of the tissue anchor of FIG. 13a;

FIG. 14b is a side elevation view of the tissue anchor of FIG. 14a;

DETAILED DESCRIPTION OF CERTAIN EMBODIMENTS

Figure 1:
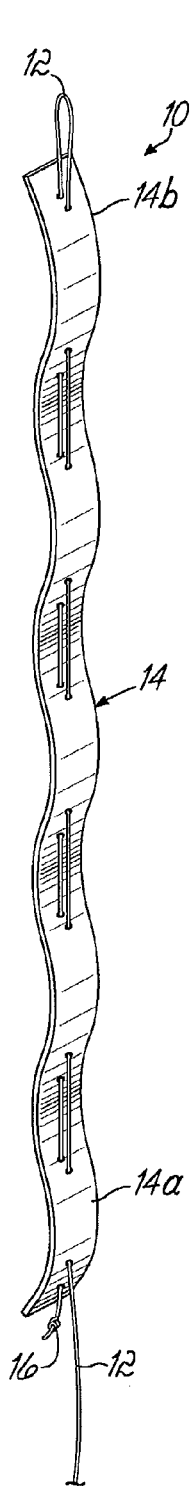
FIG. 1 is a perspective view of a tissue anchor constructed in accordance with a first embodiment of the invention.

Referring first to FIG. 1, a tissue anchor 10 constructed in accordance with a first embodiment of the invention generally includes a tensioning member 12, such as a suture, extending through spaced apart points along a flat elongate strip 14 of flexible material, such as a surgical grade fabric. It will be appreciated that the tensioning member 12 may take other forms other than suture material, such as cable or any other small diameter member having a high enough tensile strength for the intended anchoring use. The elongate strip 14 may also take various forms such as woven or nonwoven fabrics, polymers, metals or other suitable materials or combinations of materials. One or more separate pledgets or other securement members (not shown) may be used in conjunction with the elongate strip 14 for added securement and/or concealing the elongate strip 14 and, for example, thereby inhibiting blood clotting within or adjacent to the folds that will be formed in the strip 14.

A woven or nonwoven material may contain additional materials, such as threads, beads or other elements that cause at least portions of the strip 14 to be radiopaque. Currently, a surgical grade fabric constructed from polyester, such as Dacron@, is contemplated for use in constructing the strip 14. One of many possible alternative materials for use in constructing strip 14 is polytetrafluoroethylene (PTFE). Tissue anchor 10 may be partly or wholly formed from materials that are absorbed into the patient's tissue over time, depending on the intended use. The edges and/or other portions of the strip 14 may be suitably modified to prevent fraying, such as by being coated with a material that locks the fibers in place, or otherwise modified in a manner that locks the fibers at least at the edges of the strip 14 in place.

The suture 12 may extend from a proximal end portion 14a of the fabric strip 14 to a distal end portion 14b and then loop back through spaced apart points of the fabric strip 14 to the proximal end portion 14a where a knot 16 or other stop member is located for reasons to be described below. As will become apparent, the suture 12 extends through spaced apart locations along the elongate strip 14 such that tensioning of the suture 12 or other tensioning member will cause the elongate strip 14 to form folded portions 14c when the tensioning member 12 is placed under tension or pulled. Thus, the elongate strip 14 is activated in this manner between essentially an elongate deployment orientation or configuration, such as shown in FIG. 1, and a shortened configuration, such as a folded or otherwise shortened configuration having an expanded width in at least one dimension as compared to the elongate deployment configuration. It will be appreciated that the deployment orientation may take on various forms due to the flexible nature of the strip 14, especially when using a highly flexible fabric or other material. For example, a fabric material or other similarly flexible materials may be folded or otherwise deformed for carrying purposes within a catheter and/or during deployment to a tissue site and then suitably activated at the tissue site.

Figure 2A:
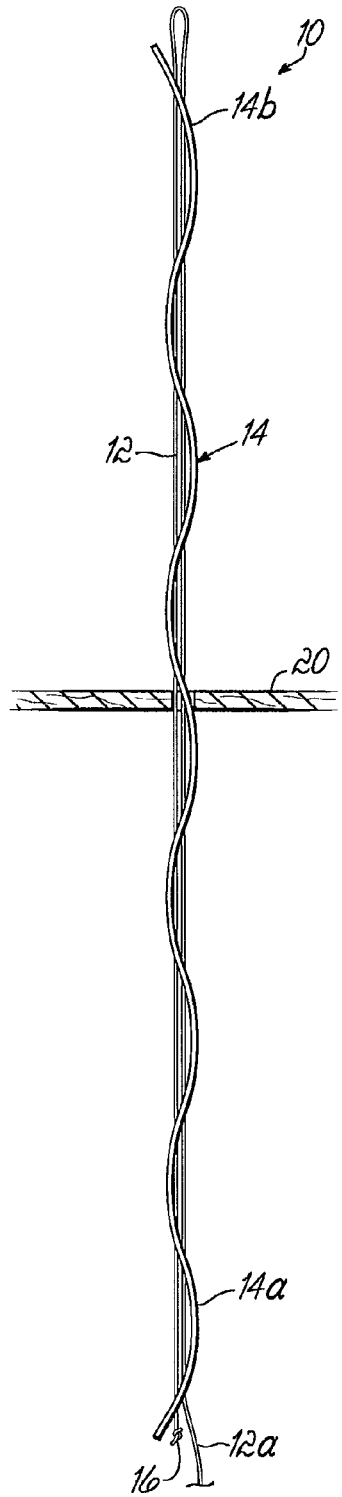
FIG. 2A is a side view of the tissue anchor shown in FIG. 1, with the tissue anchor deployed through a layer of tissue.
Figure 2B:
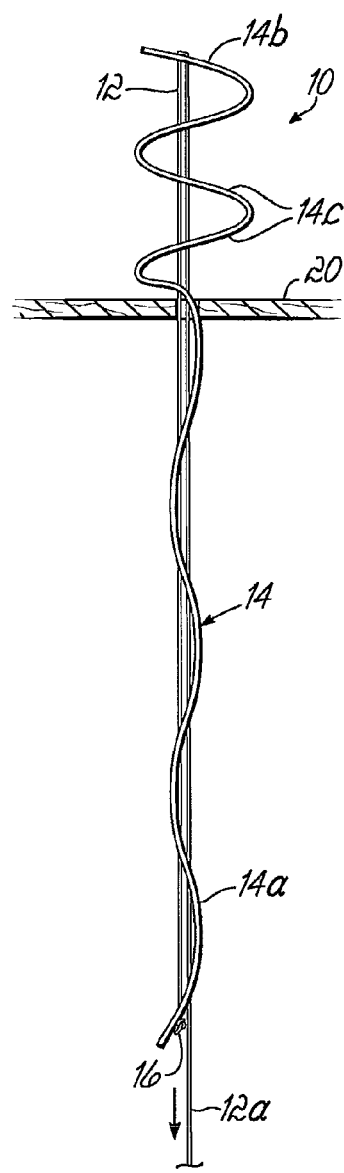
FIG. 2B is a side view similar to FIG. 2A, but illustrating the distal portion of the tissue anchor being moved toward the layer of tissue.
Figure 2C:
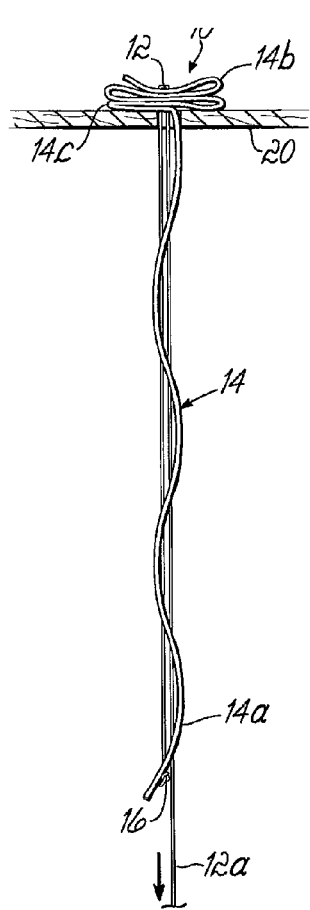
FIG. 2C is a side view similar to FIG. 2B, but showing the distal portion fully compressed and engaged against the layer of tissue.
Figure 2D:
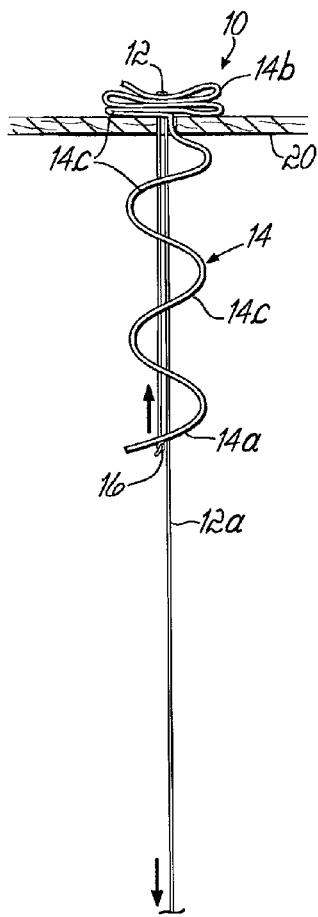
FIG. 2D is a side view similar to FIG. 2C but illustrating the proximal portion of the tissue anchor being moved toward the layer of tissue.
Figure 2E:
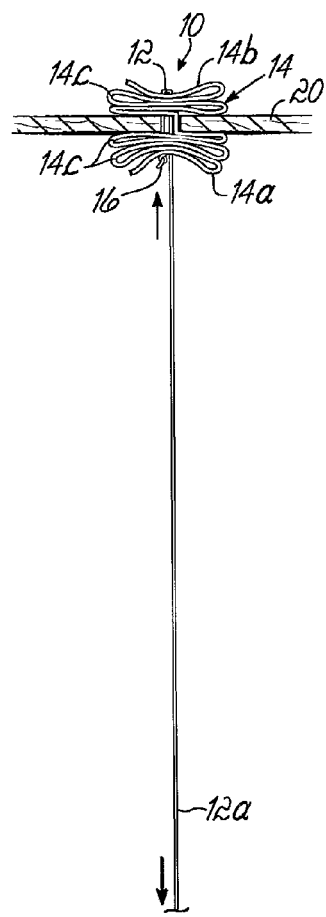
FIG. 2E illustrates the proximal and distal portions of the tissue anchor fully compressed against opposite sides of the layer of tissue.
Figure 2F:
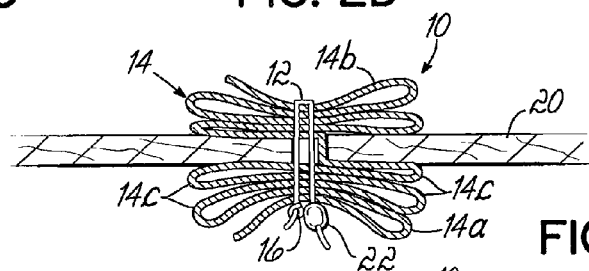
FIG. 2F is an enlarged cross sectional view illustrating the fully deployed and fastened anchor with a layer of tissue between proximal and distal anchor portions.

More specifically referring to FIGS. 2A-2E, the elongate strip 14 and attached suture 12 are initially inserted through at least one tissue layer 20 as generally shown in FIG. 2A. One end or portion 12a of the suture 12 is then pulled and thereby placed under tension. It will be appreciated that, for catheter-based procedures, suture portion 12a may extend to a location outside the patient's body for pulling or tensioning, or it may be grasped by a suitable mechanism within the catheter and pulled or tensioned. Pulling suture portion 12a may initially draw the distal portion 14b of the elongate strip 14 toward the layer of tissue 20 as shown in FIG. 2B. Once the distal portion 14b is compressed against the layer of tissue 20, the proximal portion 14a begins to be drawn and compressed against a proximal side of the tissue 20 as shown in FIGS. 2C-2E. This occurs because end 12a of the suture 12 is being pulled downwardly (as viewed for purposes of discussion in FIGS. 2C-2E) and, since the suture 12 is looped in a reverse direction through distal end portion 14b of the elongate strip 14, the knot 16 at the end of the suture 12 moves upwardly and brings the proximal portion 14a of the elongate strip 14 with it. In this manner, the proximal portion 14a of the elongate strip 14 is being folded and drawn along the suture 12 toward the layer of tissue 20 and then firmly compressed against the proximal side of the layer of tissue 20 as shown in FIG. 2E. As further shown in FIG. 2F, a suitable locker element, such as a crimp member 22, a knot or other element may be used to maintain the suture 12 and elongate strip 14 in the positions shown in FIG. 2F securely anchoring the proximal and distal portions 14a, 14b of the elongate strip 14 folded against opposite sides of the tissue 20.

Figure 3:
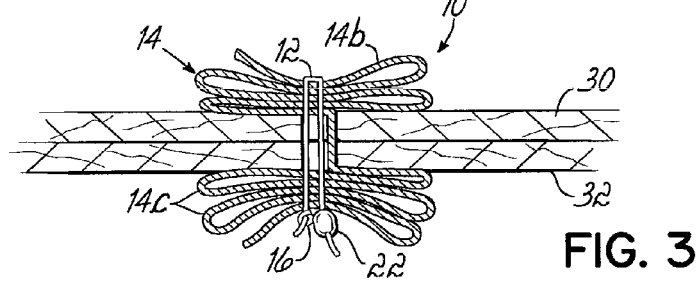
FIG. 3 is a side cross sectional view similar to FIG. 2F, but illustrating the fastening of two layers of tissue between the proximal and distal anchor portions.

As further shown in FIG. 3, the same general procedure may be used to secure two distinct tissue layers 30, 32 together by initialing extending the elongate strip 14 and tensioning member 12 through at least two layers of tissue 30, 32. In this manner, for example, two layers of tissue 30, 32 may be securely fastened together. This may, for example, involve two entirely different layers and even types of tissue or the same layer of tissue which has been folded over to effectively form two layers (i.e., portions) of tissue.

FIGS. 4A-4E schematically illustrate an annuloplasty procedure performed on a mitral valve 40 of a heart 42 utilizing tissue anchors 10 as described above in regard to the first embodiment. Performance of the annuloplasty procedure may have many variations, but is generally illustrated by the placement of at least two tissue anchors 10 and securement of the two anchors 10 together, such as with one or more tensioning members 12 therebetween. For an additional illustrative description of catheter-based annuloplasty procedures that may utilize any of the tissue anchors within the scope of the present invention, reference may be made to U.S. patent application Ser. No. 10/948,922, filed on Sep. 24, 2004, assigned to the assignee of the present invention, and the disclosure of which is hereby entirely incorporated by reference herein.

Figure 4A:
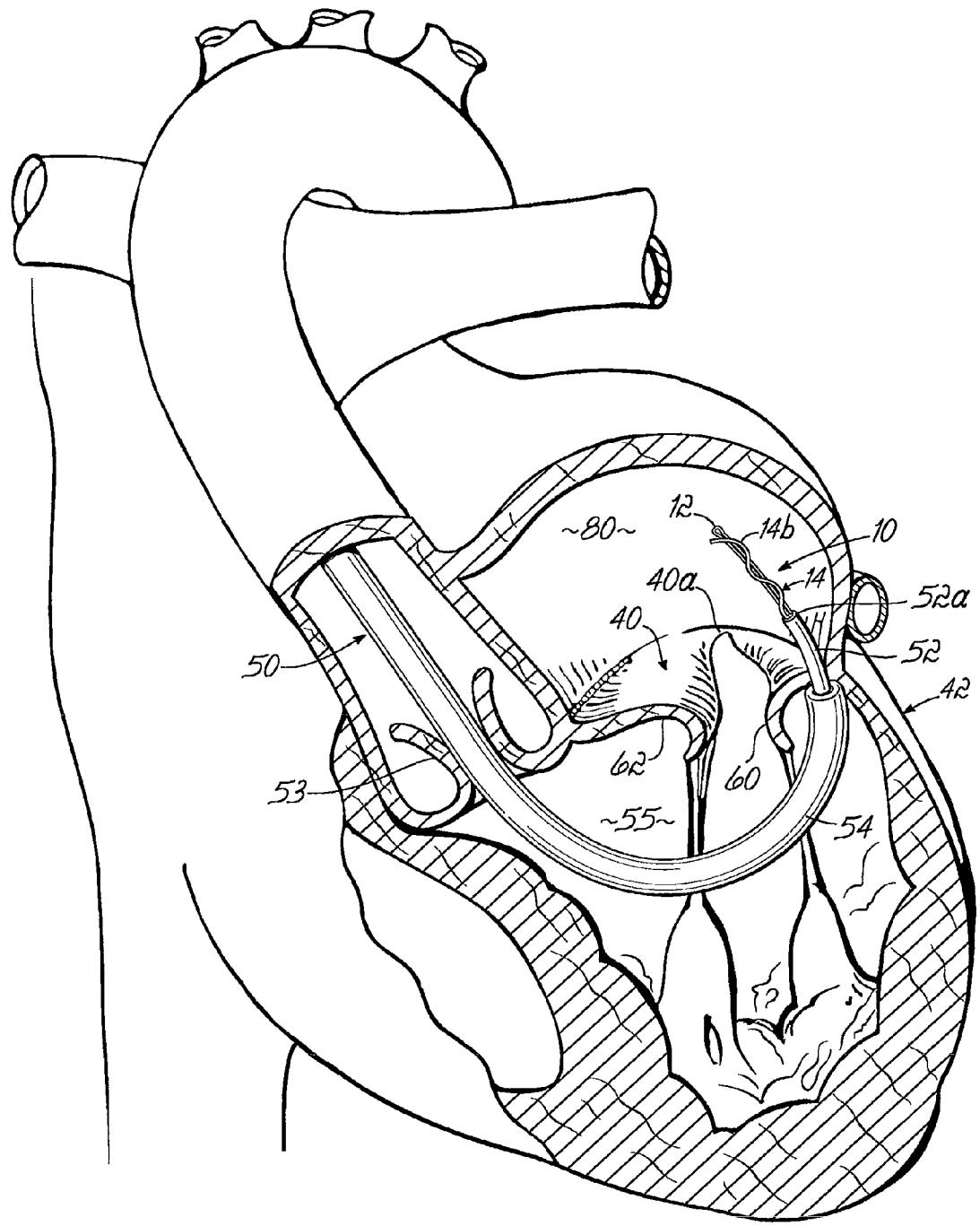
FIGS. 4A-4F are perspective views illustrating successive steps in an annuloplasty procedure on the mitral valve of a patient utilizing tissue anchors of the first embodiment.
Figure 4B:
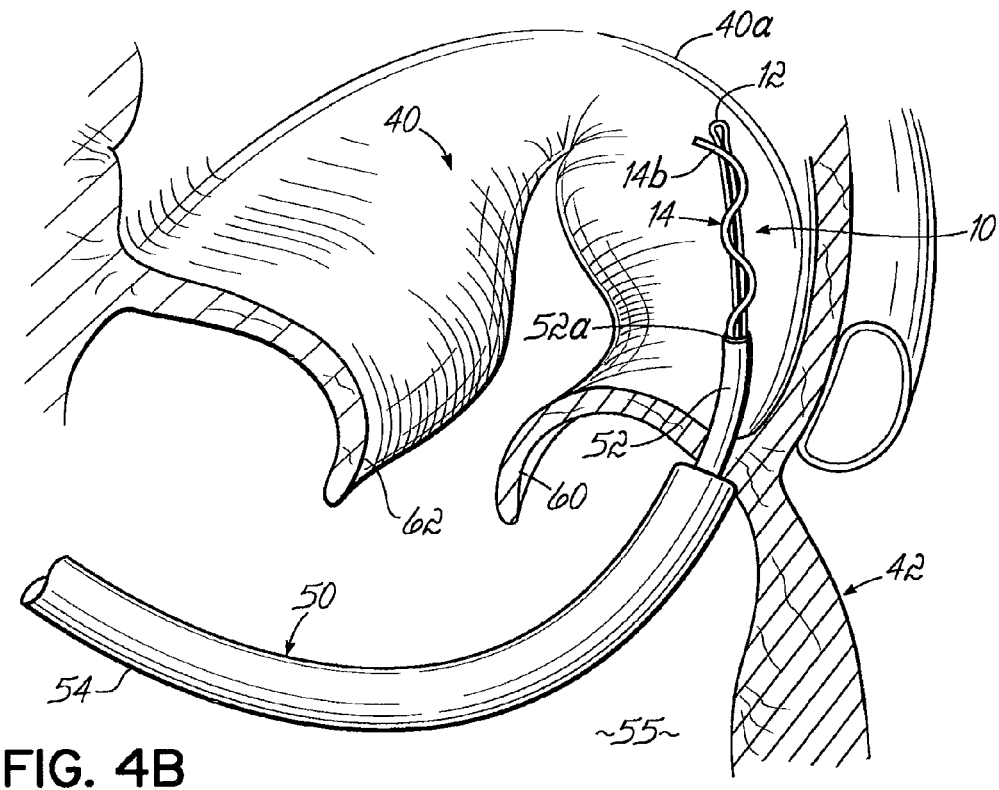
Figure 4C:
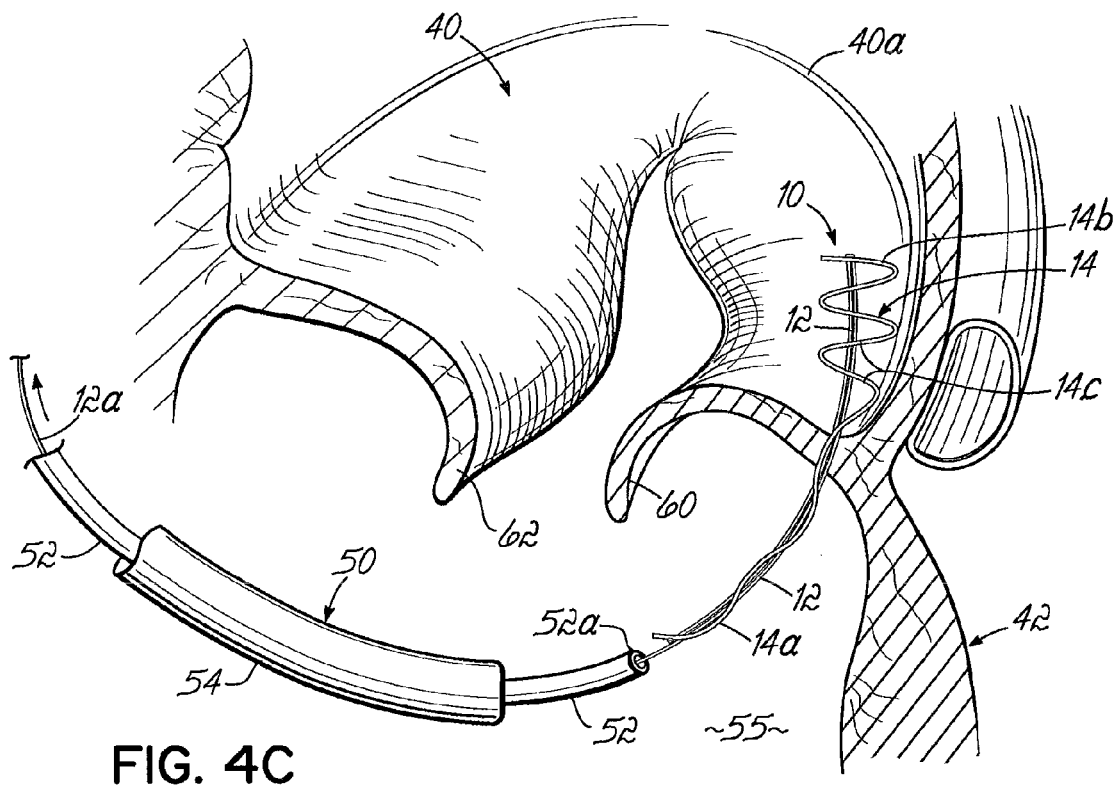
Figure 4D:
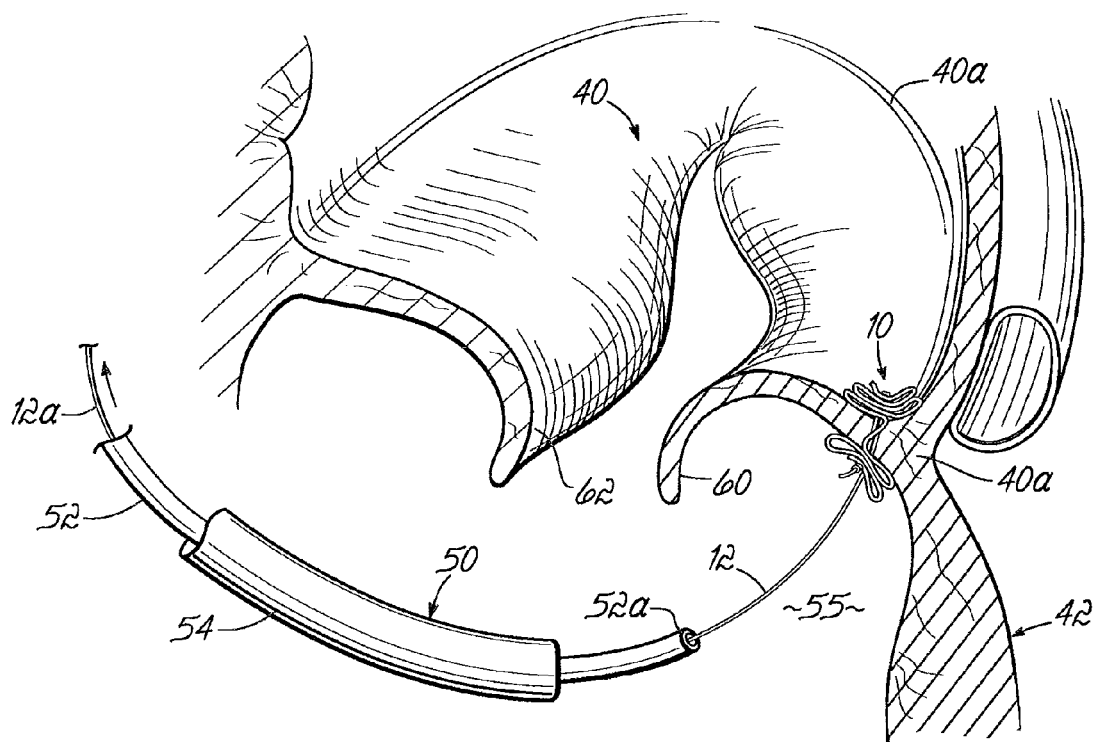

As illustrated in FIG. 4A, a first tissue anchor 10 is deployed through a catheter device 50 which may, for example, have an inner tubular member 52 or deploying catheter received within an outer tubular member 54 or delivery catheter. The tissue anchor 10 and tensioning member 12 are carried within the inner tubular member 52 and are deployed from a distal end 52a thereof. To ensure that proper force is applied to penetrate the tissue, tissue anchor 10 may be deployed or extended after the inner tubular member 52 has been inserted through tissue at the annulus 40a of the mitral valve 40. This is best illustrated in FIG. 4B. The inner tubular member 52 is withdrawn from the annulus tissue 40a either before, during or after activation of the distal end portion 14b of the elongate strip 14. As previously described, activating (e.g., compression, folding or otherwise shortening) the elongate strip 14 by pulling the suture 12 causes the distal end portion 14b and then proximal end portion 14a to be securely compressed and folded against opposite sides of the annulus tissue 40a. This procedure is repeated at least one additional time to securely fasten an additional tissue anchor 10 at a location spaced from the initial location. For example, the initial location may be at location P2 of the mitral valve annulus 40 while the second location may be spaced on either side of location P2. Catheter device 50 may be inserted into the location of annulus 40a in various manners, but is shown being inserted downwardly through the aortic valve 53 into the left ventricle 55, and curving upward toward the mitral valve annulus 40a.

Figure 4E:
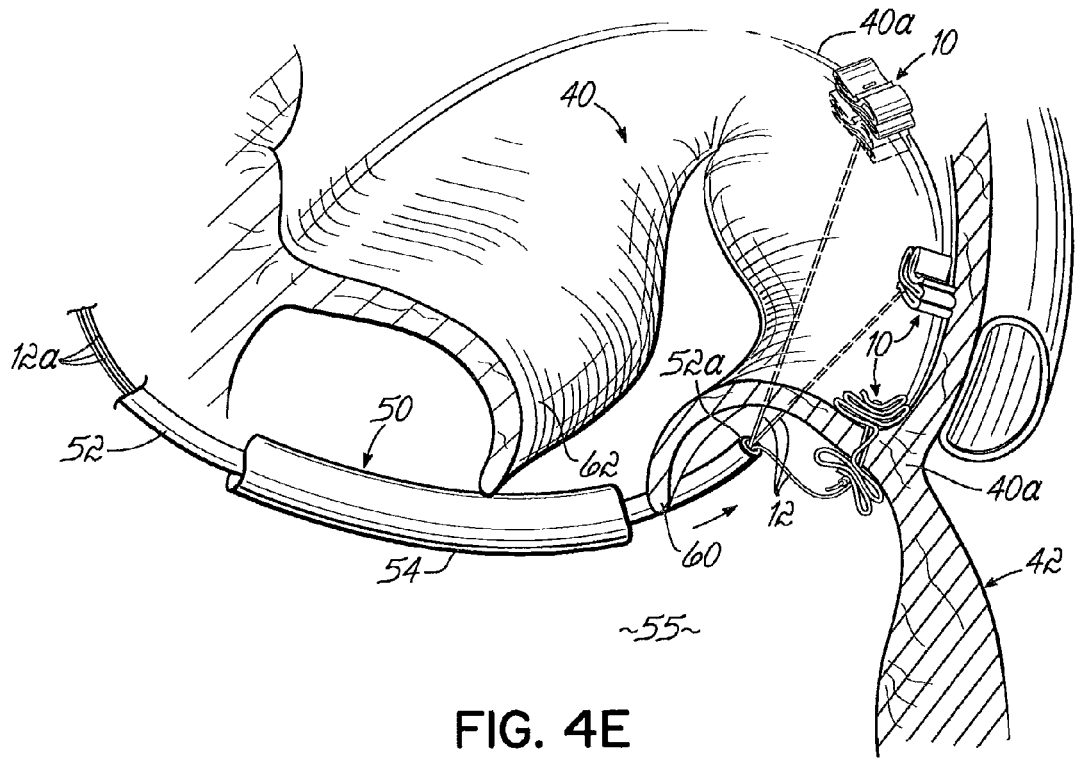
Figure 4F:
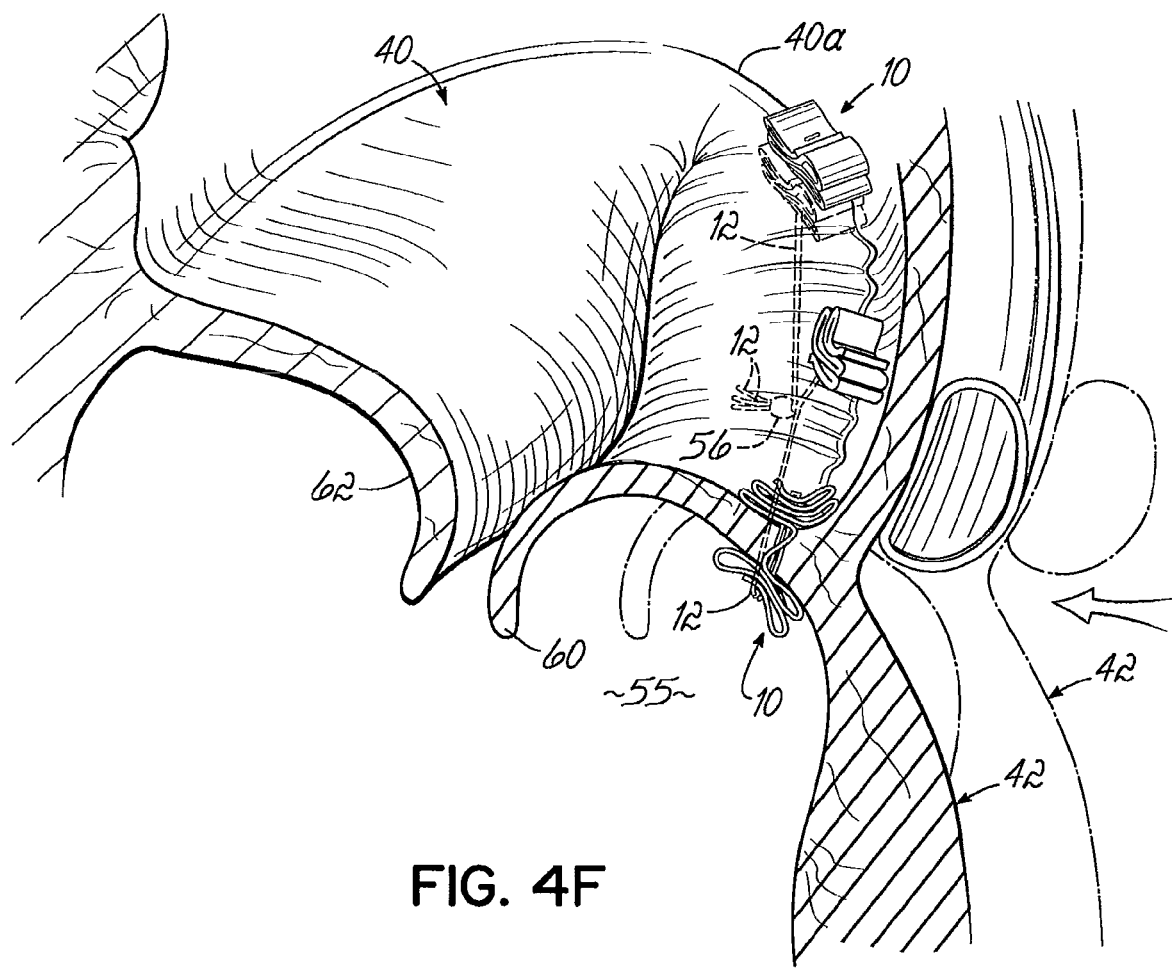

In the illustrative example shown in FIG. 4E, three tissue anchors 10 have been deployed and securely fastened to the annulus tissue 40a. As shown in FIG. 4F a suture locker 56 may then be deployed and used to maintain relative position and, therefore, tension between each of three respective tensioning members or sutures 12 associated with the three tissue anchors 10 after the tissue anchors 10 have been pulled closer to each other thereby plicating the tissue 40a between the anchors 10. This essentially shortens the valve annulus 40a and pulls the posterior leaflet 60 toward the anterior leaflet 62 to prevent leakage through the valve 40, i.e., to achieve better coaptation of the posterior and anterior leaflets 60, 62 during systole.

Figure 5A:
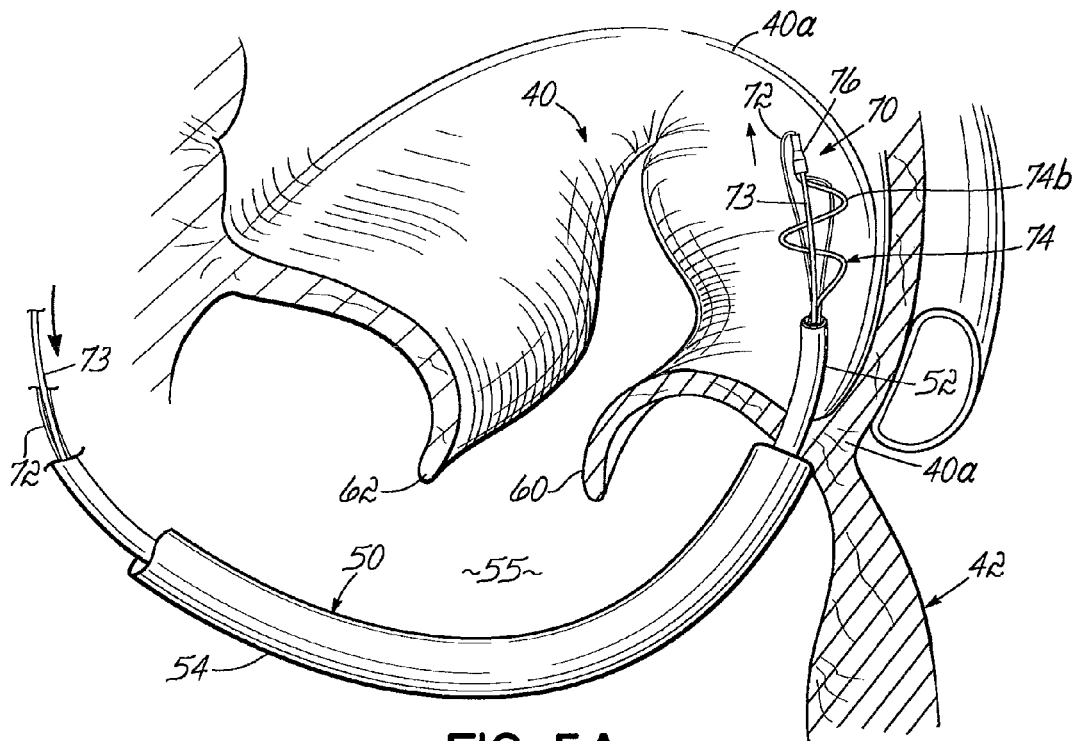
FIGS. 5A-5E are perspective views illustrating a mitral valve annuloplasty procedure utilizing tissue anchors constructed according to a second embodiment of the invention.
Figure 5B:
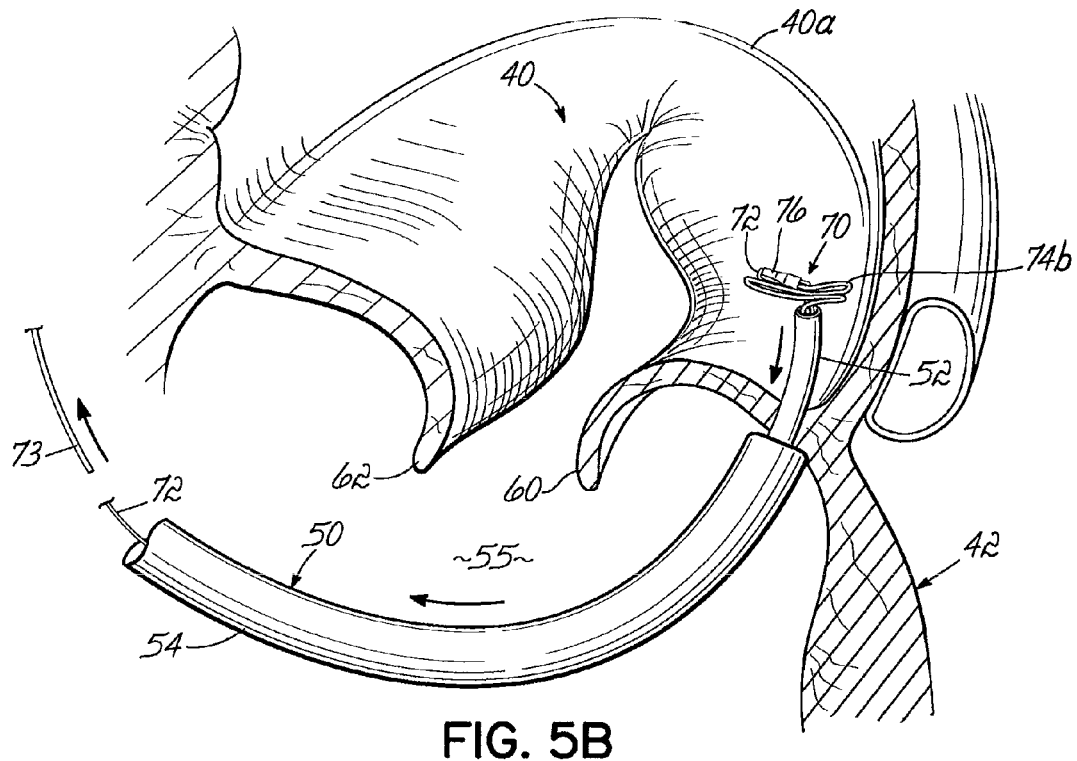
Figure 5C:
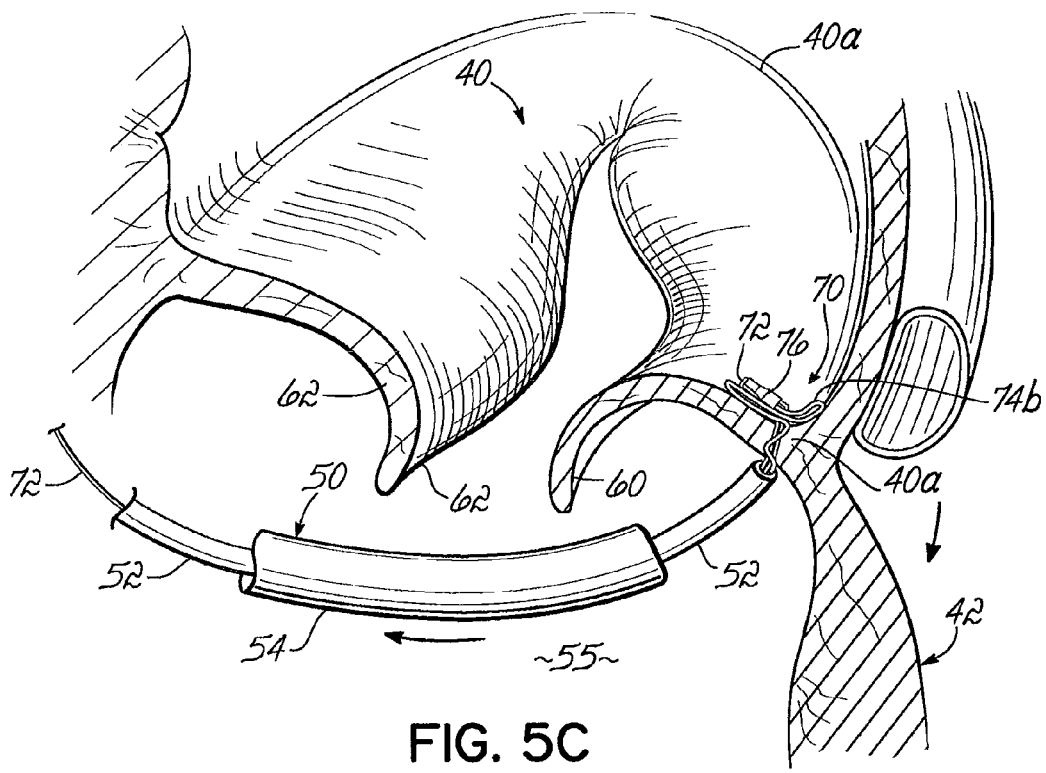
Figure 5D:
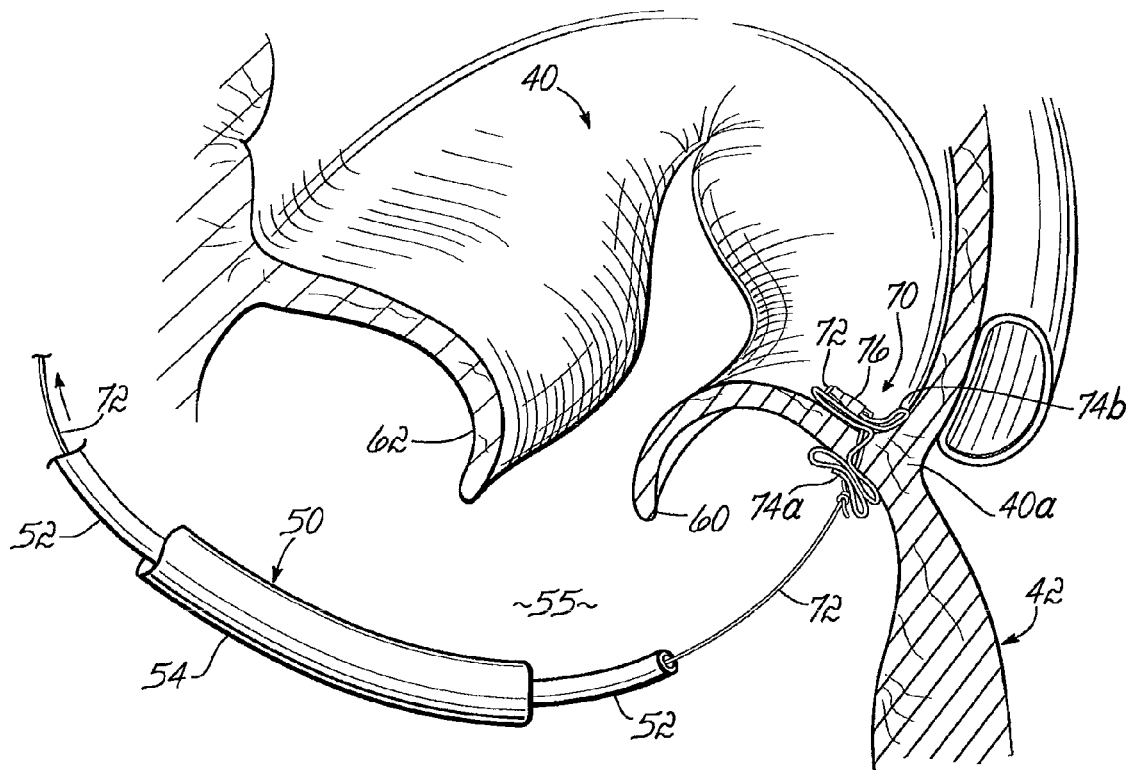
Figure 5E:
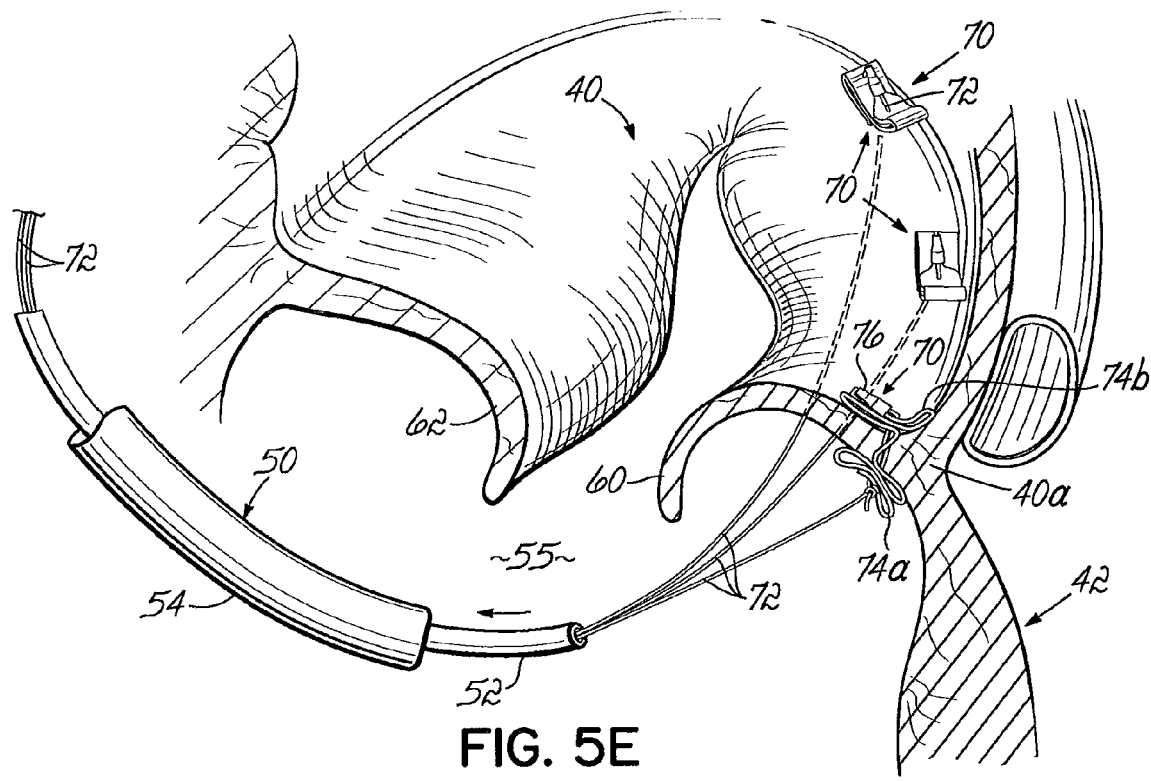

FIGS. 5A-5E illustrate a similar annuloplasty procedure on a mitral valve 40 utilizing a second embodiment of a tissue anchor 70 and a modified method of deployment and activation. In general, the differences between anchor 70 and anchor 10 will be described below with the understanding that all other attributes, options and features associated with anchor 70 may be as described above in connection with anchor 10. As shown in FIG. 5A, in this embodiment a tensioning member 72 is again used to activate a flexible, elongate flat strip 74 having proximal and distal end portions 74a, 74b. Strip 74 includes a tip 76 that is formed or otherwise secured on the distal end portion 74b. The tensioning member 72 and the tip 76 are arranged such that the tensioning member 72 slides relative to the tip 76. More particularly, the tensioning member 72 can be threaded through the tip 76. Tip 76 is made to be relatively rigid as compared to other flexible portions of strip 74 and of smaller diameter than the width of strip 74. Therefore, tip 76 helps to penetrate the annulus tissue 40a as the inner tubular member 52 and the elongate strip 74 are extended through the tissue 40a. A wire 73 may be used to push the tip 76 out of the tubular member 52 at the desired time. The tip 76 may protrude slightly from the inner tubular member 52 as the tissue 40a is penetrated to assist with piercing the tissue 40a. The tip 76 may also assist with forcing distal portion or half 74b of strip 74 into a folded or otherwise shortened configuration. To help prevent the distal portion 74b of the elongate strip from pulling back through the tissue 40a as the inner tubular member 52 is withdrawn from the annulus tissue 40a, the free end of the tensioning member 72 is pulled while the inner tubular member 52 is still penetrated through the tissue 40a and into the left atrium 80 from the left ventricle 55. This forms the distal portion 74b into a folded or otherwise shortened configuration as shown in FIG. 5B. The inner tubular member 52 may then be withdrawn without also withdrawing the elongate flexible strip 74 with it, as shown in FIG. 5C. The proximal portion 74a of the elongate strip 74 is then deployed by pulling the inner tubular member 52 further in a proximal direction, and thereby exposing the full length of strip 74. The tensioning member 72 is pulled or tensioned so as to draw and compress the proximal portion 74a of the elongate strip 74 into a folded, shortened condition against an underside of the annulus tissue 40a as shown in FIG. 5D. As with the previously described annuloplasty procedure using the first embodiment of the tissue anchor 10, this is repeated as many times as necessary to create the necessary number of tissue plications. FIG. 5E illustrates this by way of an exemplary view of three successive tissue anchor securement locations with tissue anchors 70 that may be drawn together and locked in place to achieve and retain the plications as described in connection with FIG. 4F. Such plications reduce or close the gap between the posterior and anterior leaflets 60, 62. during systole.

FIG. 6 is a side elevation view of the tissue anchor 70 as shown and described with respect to the annuloplasty procedure of FIGS. 5A-5E. This embodiment differs from the first embodiment in a number of different manners, in addition to the use of a distal tip 76 for tissue penetration purposes. For example, the elongate strip 74 is somewhat shorter than the elongate strip 14 utilized in the first embodiment. For example, the strip 74 may be about 40 mm long by about 3 mm wide. Of course, any other desired dimensions and shapes may be used depending on application needs. This may be desirable to achieve a lower profile deployed and fastened configuration with fewer folds that may lead to more versatile applications, lower incidents of blood clotting, easier use, etc. In addition, respective proximal and distal radiopaque bands 90, 92 are secured to the suture 72 at the proximal end portion of the strip 74 and to either the interior or exterior of the distal tip 76. Under a fluoroscope, these bands or other markers 90, 92 will indicate to the surgeon that the anchor 70 has been deployed, activated and fully compressed and/or fastened as necessary during the procedure. The tip 76 itself may alternatively be formed from a radiopaque material. In this second embodiment, the knot 94 formed in the suture 72 or other tensioning member is a slip knot through which another portion of the suture 72 slides during activation of the tissue anchor 70. It will be appreciated that this slip knot 94 may be replaced by another element which serves essentially the same purpose but takes the form, for example, of a small tubular element or other feature similar in function to a slip knot.

Figure 7B:
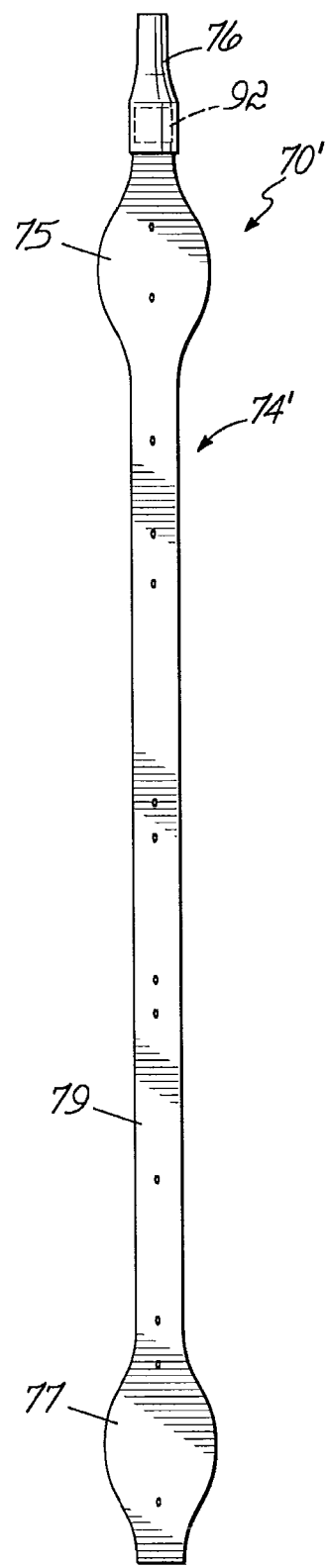
FIG. 7B is a front elevation view of an alternative anchor strip having a varying width along its length.
Figure 7C:
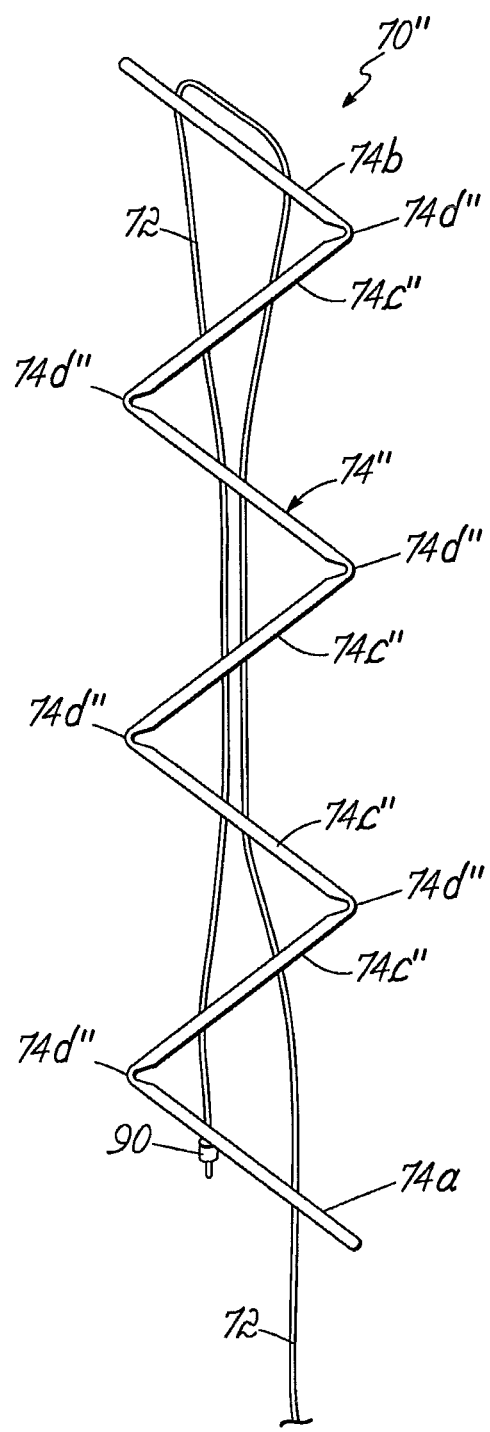
FIG. 7C is a side elevation view of another alternative anchor strip utilizing more rigid fold sections separated by living hinges.

As further shown in FIGS. 6 and 7, the tensioning member or suture 72 can advantageously extend through respective fold portions 74c of the elongate strip 74 in essentially an hourglass configuration. Specifically, adjacent portions of the suture 72 located near the proximal and distal end portions 74a, 74b of the strip 74 are spaced farther apart than the adjacent portions of the suture 72 in the middle of the strip 74. As further shown in FIG. 7A, radiopaque markers, such as distinct areas of dots 95, may be used for enabling the surgeon to visualize the folds of the elongate strip 74 during deployment and securement of the elongate strip 74. These dots or other radiopaque markers may be printed on the strip 74. For example, dots 95 or other markers may be formed with a platinum powder base ink or other suitable material that is radiopaque and biologically compatible. This radiopaque material may also add stiffness to the fold sections 74c thereby helping to maintain the fold sections 74c flat and increasing retention force on the tissue. Meanwhile, the fold lines 74d between fold sections 74c can remain highly flexible to create tight radius fold lines. As further shown in FIG. 7, each of the holes 96 that the tensioning member or suture 72 is received through may be marked by circles 98 surrounding each hole 96 or other markers for visualizing purposes during assembly of the tensioning member or suture 72 with the elongate strip 74. Optionally, holes 96 may be eliminated and the suture 72 may be threaded with a needle through the strip 74. One could also, for example, choose different sets of holes 96 along strip 74 for receiving the tensioning member or suture 72 thereby changing the width of the folds and/or number of folds and/or shape of the folds depending on the application needs or desires of the surgeon. The tensioning member or suture 72 may be threaded or otherwise attached along the strip 74 in any number of manners including, for example, x-patterns or other crossing patterns, zig-zag patterns, etc. that may alter the folded or otherwise shortened or compressed footprint of the anchor into various beneficial shapes, such as flower shapes, circular shapes or other rounded shapes, ball shapes or other configurations. Modifications of the manner in which the tensioning member or suture 72 is threaded or otherwise attached along the length of strip 74 may result in higher or lower tensioning force being required to compress the anchor and/or higher or lower friction holding force that may help maintain the anchor in the compressed or shortened configuration. The width of the elongate strip 74' may be varied along its length, such as by tapering, stepping, or forming an hourglass shape or shapes along the length of the strip 14. For example, as illustrated in FIG. 7B, having proximal and distal end portions 75, 77 of wider dimension than an intermediate or middle portion or portions 79 along the length of strip 74' will allow these wider portions 75, 77 may cover over the more intermediate folded portions 79 and prevent unnecessary contact with adjacent tissue during use. It will be appreciated that like reference numerals are used herein to refer to like elements in all embodiments and reference numerals with prime marks (') or double prime marks (") refer to like elements that have been modified in a manner as described herein or otherwise shown in the associated Figure. Strip 74 may have variable stiffness including, for example, a relatively rigid perimeter or relatively rigid edges 74e, 74f (FIG. 7) or intermittent relatively rigid sections 74c" separated by flexible sections such as living hinges 74d" (FIG. 7C) that may aid in folding and securing the elongate strip 74" into a folded condition.

Figure 8A:
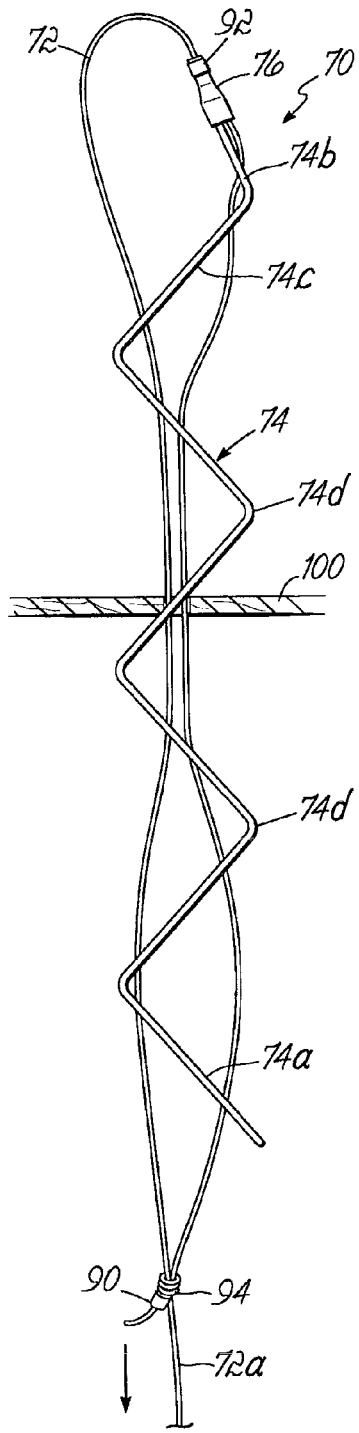
FIGS. 8A-8D are respective side views illustrating a sequence of steps used for securing the tissue anchor of the second embodiment to a layer of tissue.
Figure 8B:
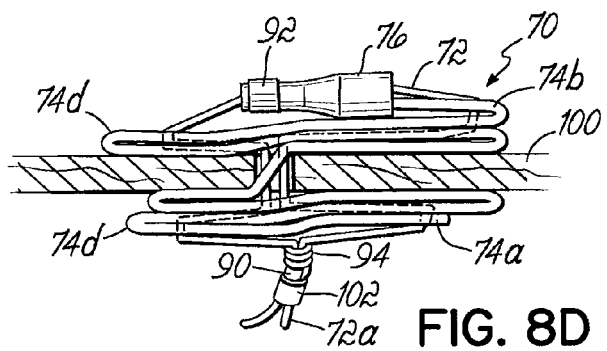
Figure 8C:
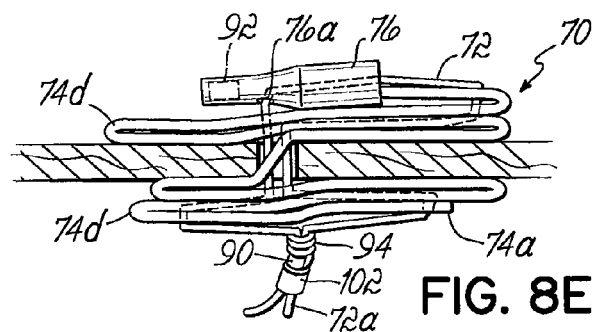
Figure 8D:
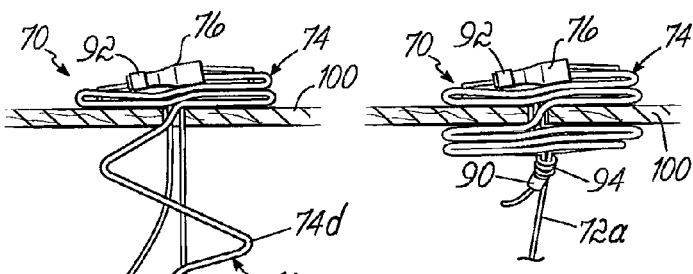
Figure 8E:
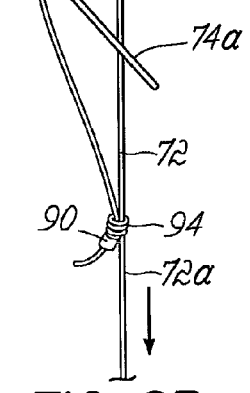
FIG. 8E is a view similar to FIG. 8D, but illustrating an alternative tip and tensioning member arrangement.

FIGS. 8A-8D illustrate a series of steps for deploying and securely fastening the tissue anchor 70 of the second embodiment to a layer of tissue 100. Generally, as shown in FIG. 8A, the combination of the elongate strip 74 and tensioning member or suture 72 is deployed through the layer of tissue 100. One end or portion 72a of the suture 72 that extends through the slip knot 94 is then pulled. This causes the distal portion 74b of the elongate strip 74 to fold and compress against the distal side of the tissue layer 100. As shown in FIG. 8B, further pulling of the tensioning member 72 causes the slip knot 94 to ride upwardly or distally along the suture 72 and against a proximal portion 74a of the elongate strip 74 thereby folding and compressing the proximal portion 74a against the proximal side of the tissue layer 100 as shown in FIG. 8C. As shown in FIG. 8D, a suitable crimp or locking element 102 may be used to securely lock the slip knot 94 in place relative to the suture or tensioning member segment which extends therethrough. This will lock the entire anchor 70 in place with the respective proximal and distal folded strip portions 74a, 74b securely retaining the tissue layer or layers 100 therebetween. FIG. 8D shows the tip 76 acting as a retainer on top of the distal end portion 74b to assist in holding the distal end portion 74b in place. FIG. 8E shows an alternative in which the tensioning member is threaded through at least one hole 76a more centrally located in the tip. Yet another alternative would be to thread the tensioning member through two centrally located holes instead of through the proximal end of the tip 76 and one centrally located hole 76a as shown in FIG. 8E. These alternatives allow the tip 76 to act more like a "T"-bar with forces acting in a more perpendicular or normal manner relative to the distal end portion 74b of the strip 74.

Figure 9A:
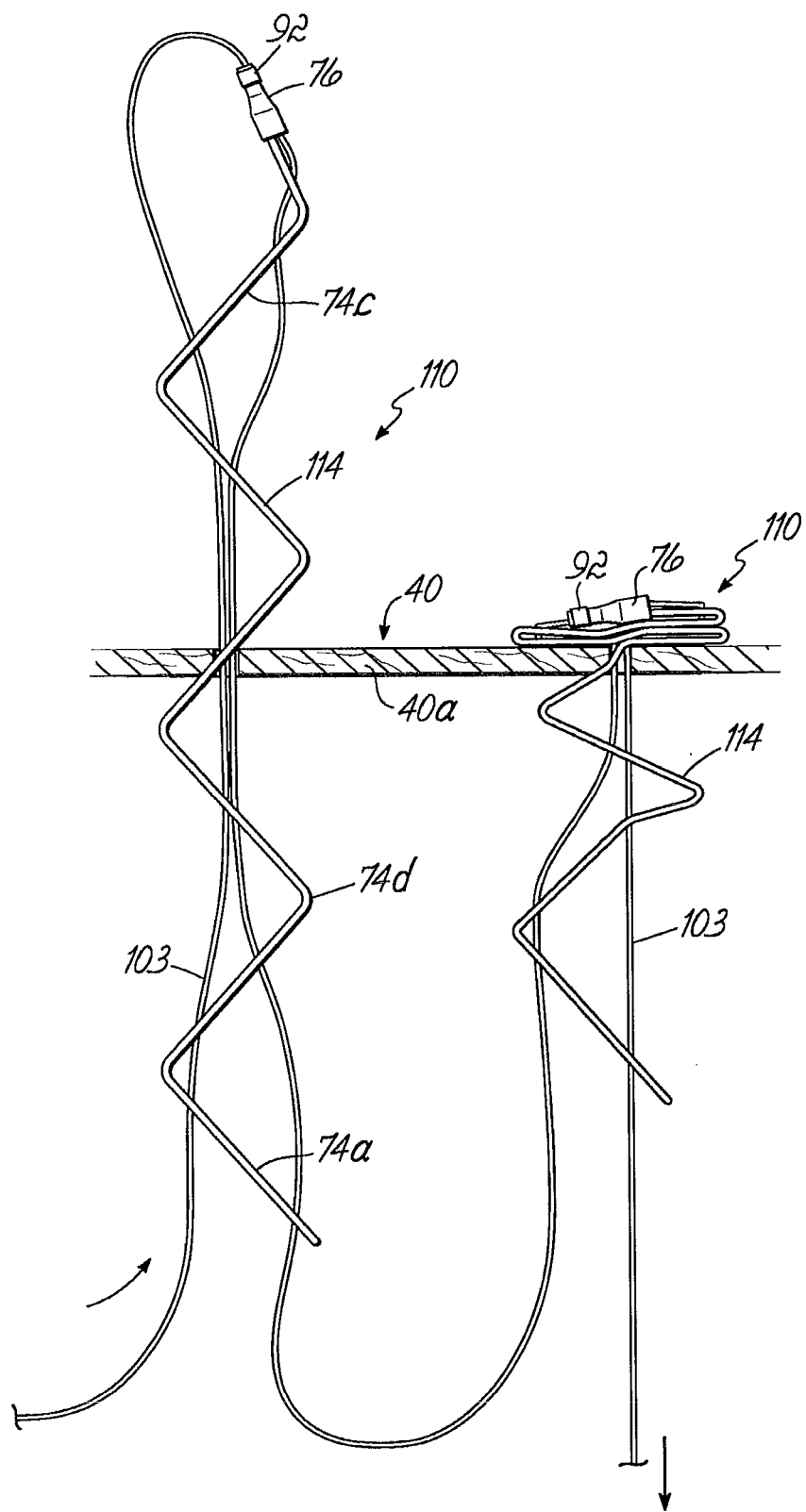
FIGS. 9A-9C are respective side elevation views illustrating an annuloplasty procedure in which two tissue anchors of the second embodiment are daisy-chained together with a single tensioning member to plicate the tissue between the anchors in a more integrated procedure.
Figure 9B:
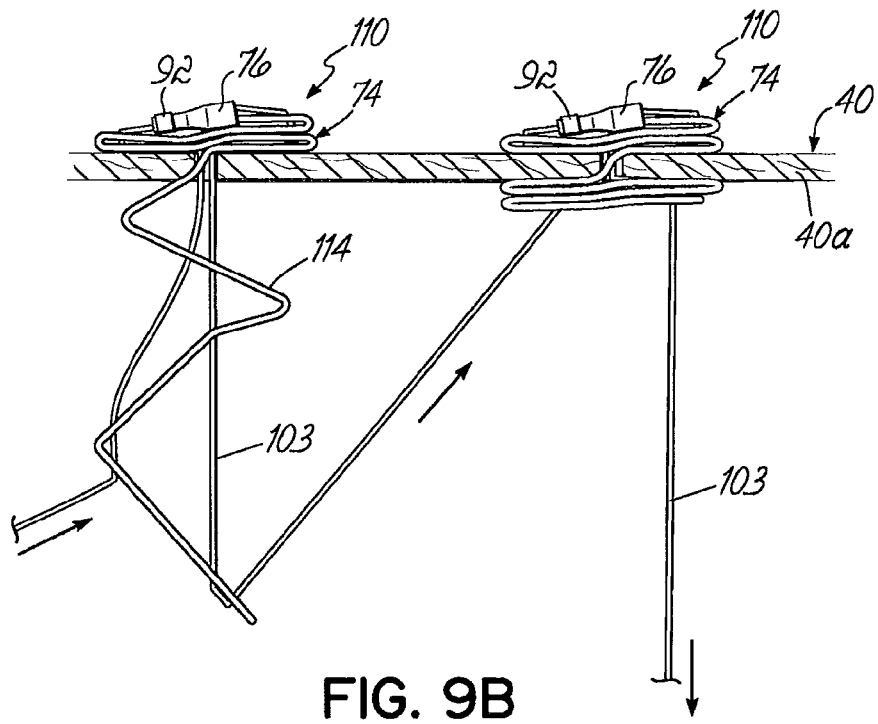
Figure 9C:
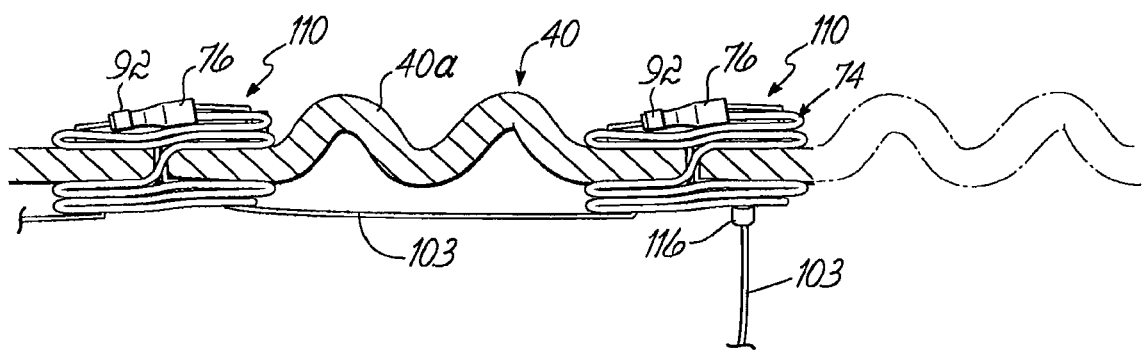

FIGS. 9A-9C illustrate another alternative embodiment of a plication procedure, for example, for use during annuloplasty on a mitral valve annulus 40a. In this regard, a single tensioning member, such as a suture 103 or other member may be used to deploy, fasten and draw together at least two separate tissue anchors 110. As shown in FIG. 9A, first and second tissue anchors 110 may be respectively deployed at spaced apart locations along the mitral valve annulus 40a. Each tissue anchor 110 includes an elongate strip 114 of flexible material, such as fabric or other material as described above, as well as a single suture 103 or tensioning member extending through each of the elongate strips 114. Upon deployment of the two tissue anchors 110 through the tissue layer 40 at spaced apart locations, the free end of the suture 103 or tensioning member is pulled thereby securely fastening the first tissue anchor 110 as shown in FIGS. 9A and 9B and subsequently securely fastening the second tissue anchor 110 to the annulus tissue 40a. Upon further pulling or tensioning of the suture 103, the tissue anchors 110 will be drawn together to plicate the tissue 40 therebetween as shown in FIG. 9C. A crimp or other locker member 116 may then be used to lock in the desired amount of plication by crimping onto the free end of the suture 103 adjacent to the slip knot 94 of the first tissue anchor 110 as shown in FIG. 9C. The free end of the suture 103 may then be cut to eliminate or reduce the length of the suture tail.

Figure 10A:
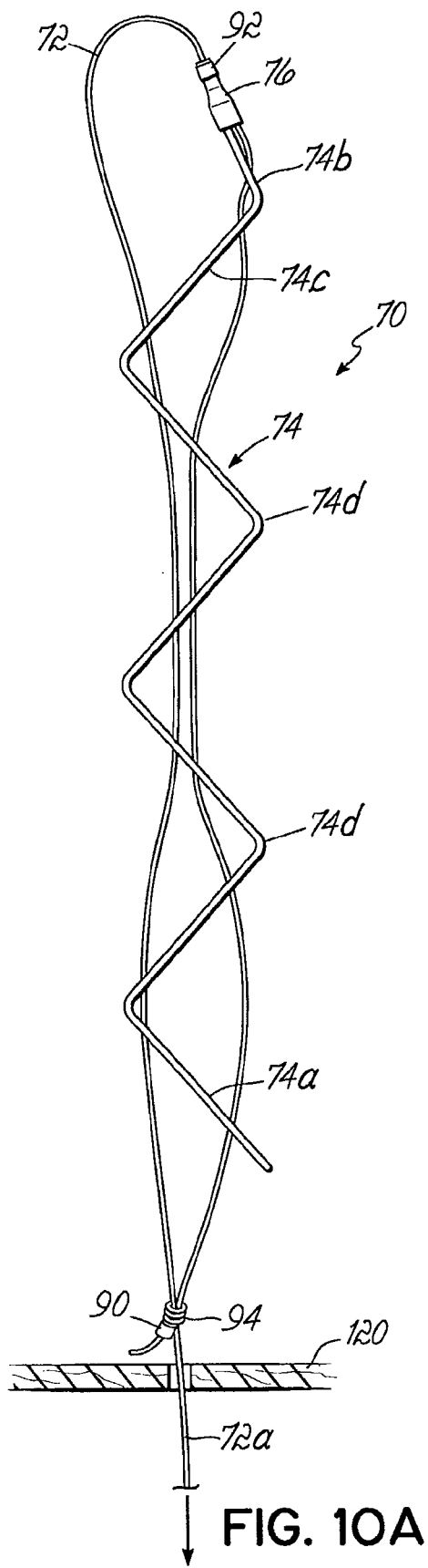
FIGS. 10A and 10B are respective side elevation views illustrating the tissue anchor of the second embodiment used to provide an anchor or securement location on only one side of a tissue layer.
Figure 10B:
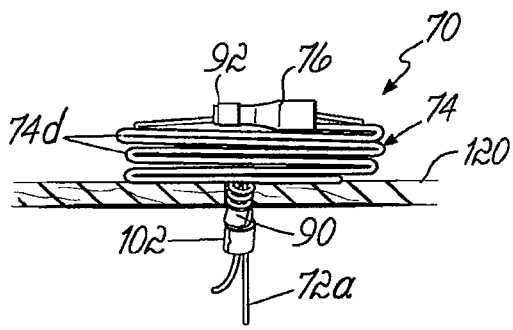

FIGS. 10A and 10B illustrate a tissue anchor 70 of the second embodiment, for example, being used to provide an anchor or securement location on only one side of a tissue layer 120. In this regard, the tissue anchor 70 may be extended entirely through the tissue layer(s) 120. The free end of the suture or tensioning member 72 is then pulled proximally to compress and fold the elongate strip 74 against the distal side of the tissue layer 120 as shown in FIG. 10B. It will be appreciated that activation of strip 74 occurs similarly to the other described embodiments, except that the activated portion (that is, the folded or otherwise shortened portion) is located entirely on one side of the tissue layer 120. As illustrated, the intermediate or middle portion between the proximal and distal end portions of the anchor member shortens to adjust to the amount of tissue contained therebetween (if any) or shortens during the compression process on only one side of the tissue.

Figure 11A:
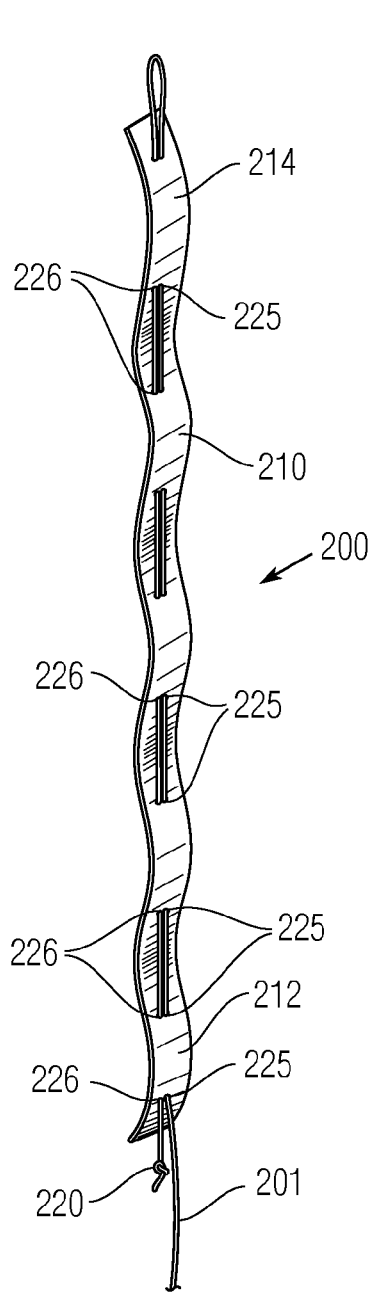
FIG. 11a is a perspective view of an exemplary tissue anchor in accordance with the present teachings.

FIG. 11a illustrates another exemplary tissue anchor of the present teachings. In various embodiments, the tissue anchor includes at least one elongated strip. In some embodiments, the tissue anchor has an elongated delivery configuration where the elongated strip is relaxed and extended. In some embodiments, the tissue anchor has a deployed configuration when the elongated strip is folded or otherwise shortened.

In various embodiments, the tissue anchor includes at least one tensioning member. In some embodiments, the tensioning member causes both ends of the elongated strip to move toward each other. This motion can create a shortened distal portion and/or a shortened proximal portion. In certain embodiments, doing so secure the tissues between the distal and the proximal portions of the elongated strip.

In various embodiments, a clinician deploys a plurality of tissue anchors along a tissue and plicates the tissue between the tissue anchors by reducing the distance between the tissue anchors. In some embodiments, tissue anchors of the present teachings is used percutaneouly. For example, the tissue anchors are delivered percutaneously. In other embodiments, tissue anchors of the present teachings are used in open-heart surgeries.

According to various embodiments of the present teachings, the tensioning member is in the form of a suture. The term "suture" used herein can be a strand, a wire, a cord, a fiber, a yarn, a filament, a cable, a thread, or the like, and these terms may be used interchangeably. It will be appreciated that the tensioning member may take forms other than a suture, such as any other small-diameter members having a suitable tensile strength for the intended anchoring use.

According to various embodiments of the present teachings, the elongated strip is made of a flexible material. In some embodiments, the flexible material is a surgical grade fabric. The elongated strip may also take various forms such as woven or nonwoven fabrics, polymers, metals, other suitable materials, or combinations thereof. For example, the surgical grade fabric used in various embodiments of the present teachings can be constructed from a polyester, such as Dacron, RTM, PTFE, UHMPE, HDPE, polypropylene, polysulfone, or other biocompatible plastic. In various embodiments, the flat elongated strip causes a tissue response, for example, tissue growth. In some embodiments, the surface finish of the strip is textured to induce tissue response and tissue in-growth for improved stabilization. In other embodiments, the strip comprises porous materials to promote tissue in-growth. In yet other embodiments, the strip comprises one or more compounds that address issues associated with the product performance. For example, the one or more compounds can be embedded in the strip. In certain embodiments, the one or more compounds are released over time after implantation. These compounds can reduce calcification, protein deposition, thrombus formation, or a combination of some or all of these conditions. The one or more compounds can also be used to stimulate a biological response, for example, to induce tissue in-growth. In some embodiments, the compound is an anti-inflammatory agent. In some embodiments, the compounds reduce tissue proliferation adjacent to the device. One with ordinary skill in the art would understand that numerous agents are available for the above applications and can select such an agent without undue experimentation for each of the applications.

In various embodiments, one or more of the edges and/or other portions of the strip are modified, for example, to prevent from fraying. In some embodiments, one or more of the edges or other portions of the strip are coated with a material that locks the fibers in place. Other methods can also be used to lock the fibers at one or more edges of the strip in place.

Figure 11B:
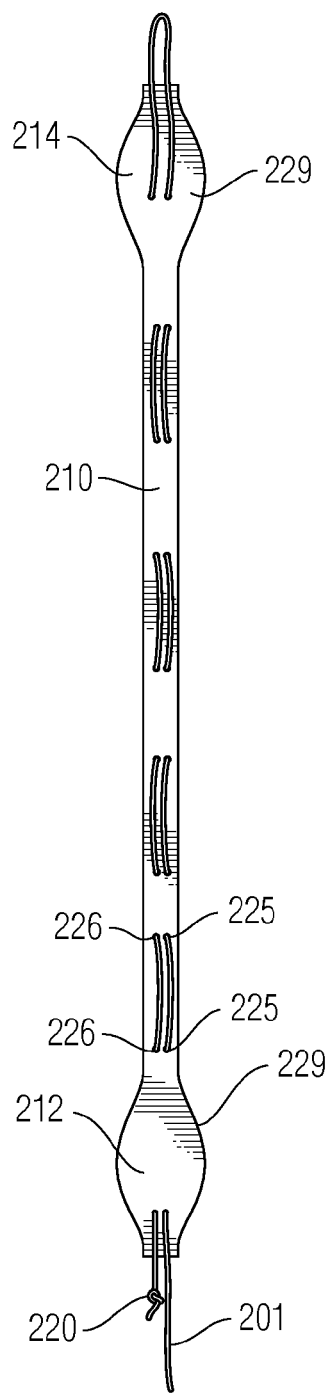
FIG. 11b is a perspective view of an exemplary tissue anchor in accordance with the present teachings.

In various embodiments, the elongated strip has a rectangle profile as illustrated in FIG. 11a. In other embodiments, the elongated strip has a hour glass profile as illustrated in FIG. 11b. One skilled in the art would understand that the elongate strip can have other profiles, and accordingly the embodiments discussed herein are not limiting to the scope of the present teachings.

In various embodiments, one or both of the tensioning member and the elongated strip are made of a resorbable polymer. In some embodiments, such a resorbable polymer is polyactic acid, polyglycolic acid, polycaprolactone, or combinations thereof. Other resorbable polymers that are known to those skilled in the art can also be used without undue experimentation and thus are within the scope of the present teachings. In various embodiments, the material that is used to make the tissue anchor is multilayered. For example, the material can include a coating of resorbable polymer. It can include a semipermeable polymer that optionally is impregnated with one or more of the compounds discussed herein. In certain embodiments, the one or more compounds is released in a controlled manner.

In various embodiments, the flat elongated strip also includes a radiopaque marker. The radiopaque marker can be in the form of threads, beads, or other forms. Without limiting the scope of the present teachings, the radiopaque marker allows the strip to be visualized by using a radiographic imaging equipment using x-ray, magnetic resonance, ultrasound, fluoroscopic, or other visualization techniques. In some embodiments, markers are attached to the strip. For example, the radiopaque markers can be wrapped, laminated, and/or bonded through a welding process. An adhesive such as cyanoacrylate or other adhesives known to those skilled in the art can also be used to attach a radiopaque marker to the strip.

In various embodiments, the radiopaque markers protrude out of or are flush with the implant. In some embodiments, the radiopaque marker is made of titanium, tungsten, platinum, irridium, gold, alloys of these materials. Other materials that are known to those skilled in the art can also be used. In other embodiments, the radiopaque markers each comprises cobalt, fluorine, or other paramagnetic materials. In yet other embodiments, the radiopaque markers each comprises other MR visible materials that are known to those skilled in the arts. In various embodiments, the radiopaque markers are arranged on the implant in a pattern.

Referring to FIG. 11a, a tissue anchor 200 constructed in accordance with some embodiments of the present teachings generally includes a tensioning member 201 extending from a proximal end portion 212 of a flat elongated strip 210 to a distal end portion 214 and then looping back to the proximal end portion 212 through a plurality of openings along the flat elongated strip 210. In some embodiments, one end of the tensioning member 201, after it extends from the proximal end to the distal end and loops back to the proximal end of the strip 210, forms a knot 220 around the other end portion of the tensioning member 201. In some embodiments, the knot 220 slides along the other end portion of the tensioning member 201 in such way that it pulls the free end of the tensioning member 201 proximally, causing the knot 220 moving distally and shortening the longitudinal length of the strip 210. By doing so in these embodiments, the elongated strip 210 is folded and the ends of the strip 210 are drawn toward each other. In certain embodiments, the flat elongated strip 210 also can include at least one pre-set folding line (not shown) which allows the flat elongated strip 210 to be fold at the pre-set folding line.

As seen in FIG. 11a, in various embodiments, the elongated strip has two sets of openings 225, 226 (first openings 225 and second openings 226). In some embodiments, the tensioning member 201 extends from the proximal end portion 212 of the strip 210 to the distal end portion 214 of the strip 210 through the first set of openings 225. Upon reaching the distal end of the elongated strip 210, in some embodiments, the tensioning member 201 loops back and further extends from the distal end portion of the strip 210 to the proximal end of the strip through the second set of openings 226.

In certain embodiments, as shown in FIG. 11a, the tensioning member 201 extends from the proximal end of the strip 210 distally, travels from one side of the strip 210 to another side by passing through the first opening 225 closest to the proximal end of the strip 210 in the first set of openings 225; the tensioning member 201 further extends distally, passes through the next opening 225 distal to the first opening 225 in the first set of openings 225. The tensioning member extends further distally repeating above steps until it passes through the last opening 225 in the first set of openings 225 and reaches the distal end of the strip 210. In one embodiment of the present teachings, there are ten openings 225 in the first set of openings 225. Strips 210 having between four and twelve openings 225 in the first set of openings can be made and used by one with ordinary skill in the art without undue experimentation.

In various embodiments of the present teachings, upon reaching the distal end of the strip 210, the tensioning member 201 loops back, extends proximally, travels from one side of the strip 210 to another side by passing through the first opening 225 closest to the distal end of the strip 210 in the second set of openings 226. The tensioning member 201 further extends proximally, travels to the first side of the strip 210 by passing through the next opening 226 proximal to the first opening 226 in the second set of openings 226. The tensioning member 201 extends further proximally repeating the above steps until it passes through the last opening 226 in the second set of openings 226 and reaches the proximal end of the strip 210. In some embodiments of the present teachings, there are ten openings 226 in the second set of openings 226. Elongated strips 210 having between four and twelve openings 226 in this set can be made and used by one with ordinary skill in the art without undue experimentation.

In various embodiments of the present teachings, as illustrated in FIG. 11a, the tensioning member 201 extends from one side of the strip 210 distally, loops back, and ends on the same side of the strip 210. In other embodiments, the tensioning member 201 extends from one side of the strip 210 distally, loops back, and ends on a different side of the strip 210.

In various embodiments of the present teachings, the number of openings 225 in the first set and the number of openings 226 in the second set are the same as illustrated in FIG. 11a. In other embodiments, the number of openings 225 in the first set and the number of openings 226 in the second set are different.

Figure 11C:
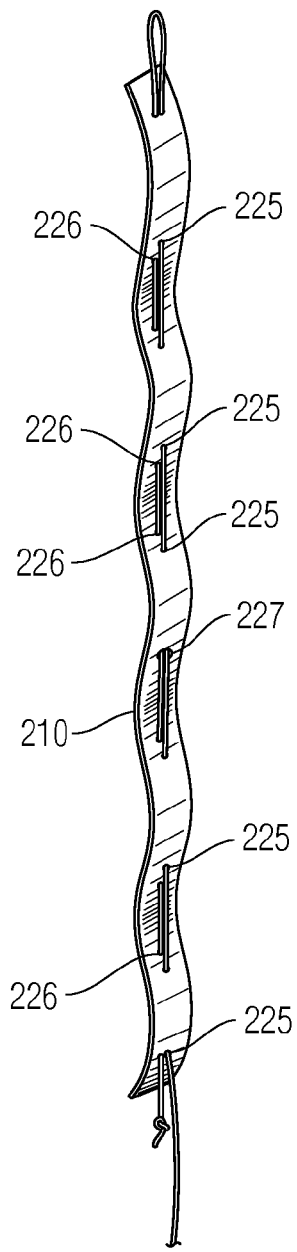
FIG. 11c is a perspective view of an exemplary tissue anchor in accordance with the present teachings.

In some embodiments, the first and second sets of openings 225, 226 are different as illustrated in FIG. 11a. In another embodiment, the first and second sets of openings 225, 226 share at least one opening as illustrated in FIG. 11c. This common opening is identified with reference character 227 in FIG. 11c.

As mentioned above, the strip 210 can have an hour glass profile as illustrated in FIG. 11b. In this embodiment, the strip 210 has a pair of sections 229 of increased width (with one being located at the proximal end portion 212 and one at the distal end portion 214).

According to various embodiments of the present teaching, at least one opening 225 in the first set of openings 225 has a corresponding opening 226 in the second set of openings 226 and together they form a pair of openings on the strips 210. In some embodiments, at least one pair of openings 225, 226 form a line perpendicular to the longitudinal axis of the strip 210. In other embodiments, at least one pair of the openings 225, 226 forms a line parallel to the longitudinal axis of the strip 210. In yet other embodiments, at least one pair of the openings 225, 226 form a line that forms an angle with the longitudinal axis of the strip 210 as illustrated. In some embodiment, lines formed by all of the pairs of openings 225, 226 are in the same orientation with each other. For example, they can be parallel to one another and/or perpendicular to the longitudinal axis of the strip 210 as illustrated in FIG. 11a. In another example, they can all be parallel to the longitudinal axis of the strip 210. In yet other examples, the lines formed by all the pairs of openings 225, 226 can have random directions.

In various embodiments, the two openings 225, 226 in a pair are 2-3 mm apart from each other. In some embodiments, the distance between two opening 225, 226 is the same in each pair. In some embodiments, the distance between two openings 225, 226 is different from one pair to another.

In various embodiments, the distance between two adjacent openings 225, 225 (or 226, 226) in the same set, defined by the distance from one opening to the next closest one in the same set of openings (either 225 or 226), is about 5-12 mm. In some embodiments, the distances between each adjacent openings 225, 225 (or 226, 226) is the same as each other. In some embodiments, the distances between each adjacent openings is different from each other.

In various embodiments, at least one pair of the openings 225, 226 are at the lateral center of the strip. In some embodiments, all the pairs of openings 225, 226 are at the lateral center of the strip. In some embodiments, at least one pair of the openings 225, 226 is biased toward one side of the strip 210. In some embodiments, all the pairs of openings 225, 226 are biased toward the same side of the strip. In some embodiments, each of the pairs of openings is biased toward different sides of the strip 210.

In various embodiments, all the openings 225, 226 in at least one set of openings, or in both the sets of openings, form a straight line. In various embodiments, all the openings in at least one set of the openings, or in both the sets of openings, form a curved line.

Figure 12A:
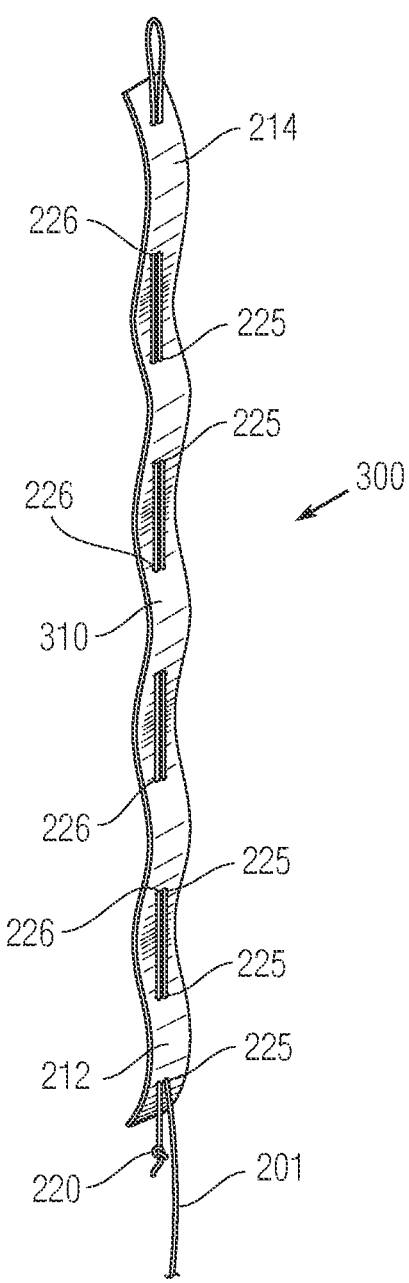
FIG. 12a is a perspective view of an exemplary tissue anchor in accordance with the present teachings.
Figure 12B:
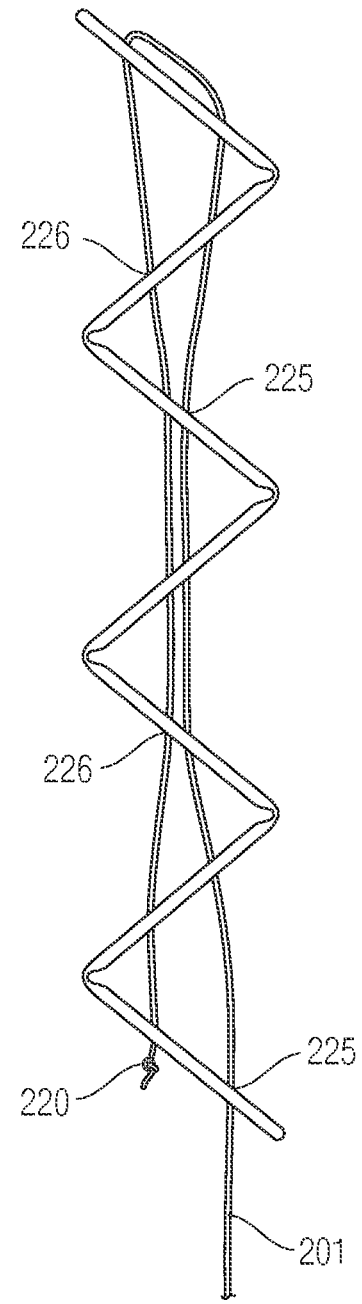

FIGS. 12a and 12b illustrate an exemplary elongated profile of an exemplary tissue anchor 300 that includes an elongated strip 310 and wherein the openings 225 in the first set of openings 225 form a straight line parallel to the longitudinal axis of the strip 310, and the openings 226 in the second set of openings 226 form another straight line parallel to the longitudinal axis of the strip 310 and at a distance from the line formed by the first set of openings 225. FIG. 12b is a side elevation view of the strip 310 showing the routing of the tensioning member 201 through the strip 310.

Figure 13A:
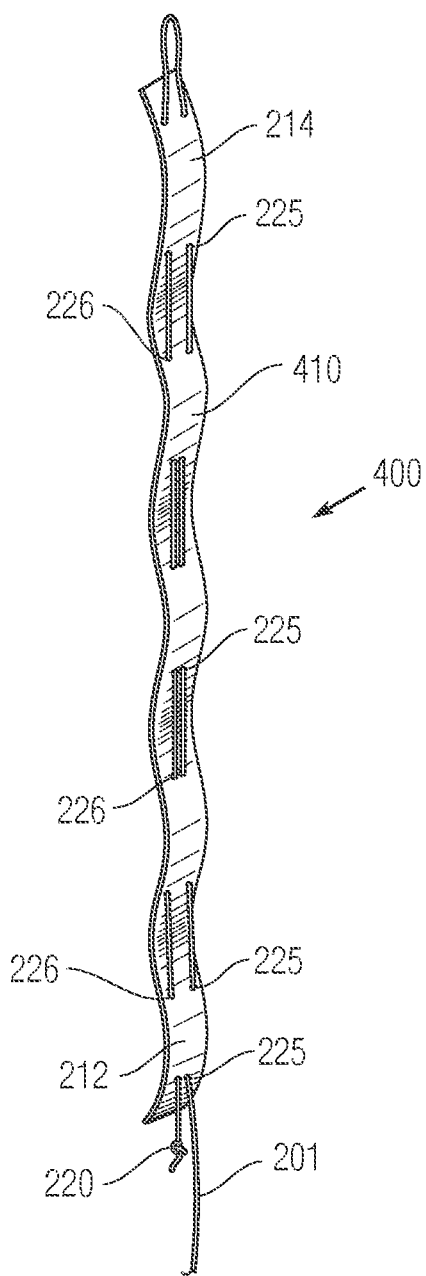
FIG. 13a is a perspective view of an exemplary tissue anchor in accordance with the present teachings.
Figure 13B:
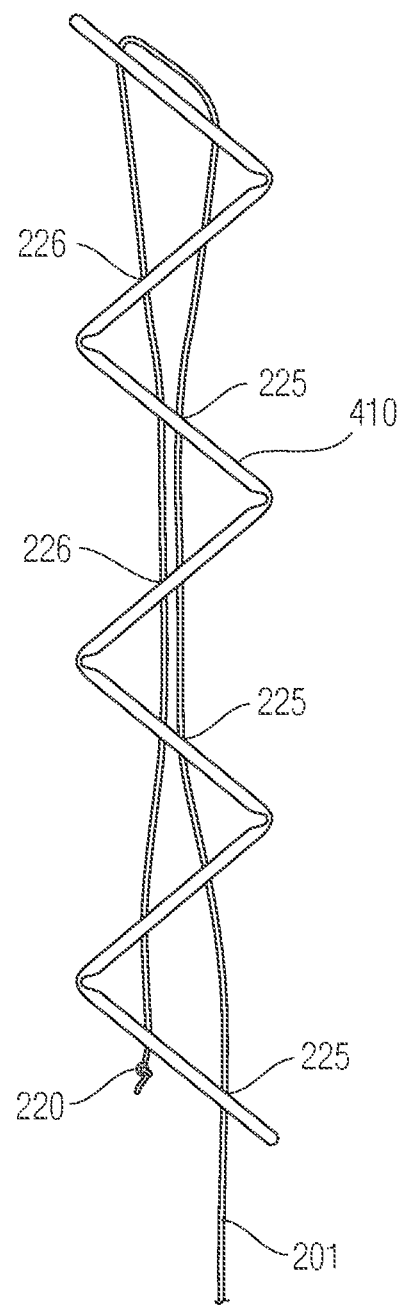

FIGS. 13a and 13b illustrate an exemplary elongated profile of an exemplary tissue anchor 400 that includes an elongated strip 410. The openings 225 in the first set of openings form a curve with the openings 225 in the middle portion of the strip closest to the lateral center of the strip 410, and the openings 226 in the second set of openings form another curve with the openings 226 in the middle portion of the strip 410 closest to the lateral center of the strip 410, and the two curves have a lateral distance from each other and together form an "hour glass" shape. FIG. 13b is a side elevation view of the strip 310 showing the routing of the tensioning member 201 through the strip 310.

Figure 14A:
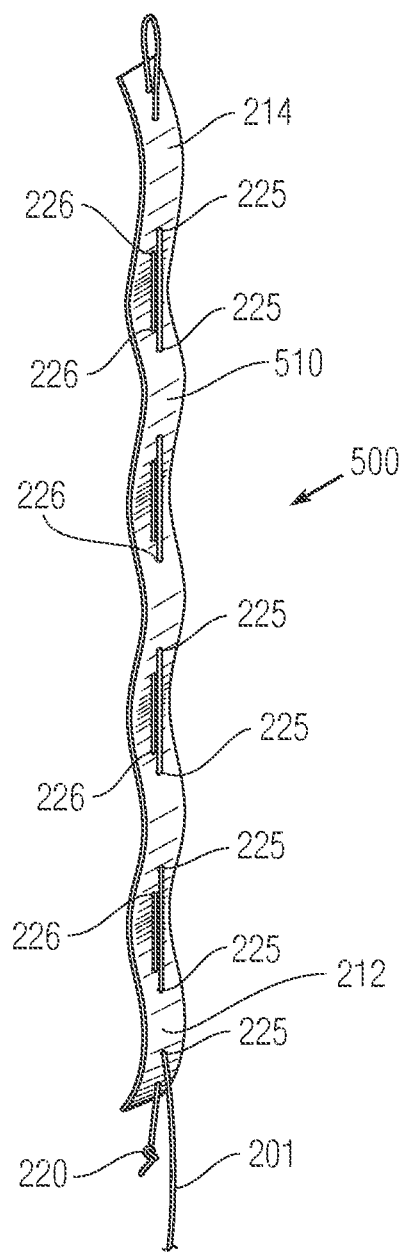
FIG. 14a is a perspective view of an exemplary tissue anchor in accordance with the present teachings.
Figure 14B:
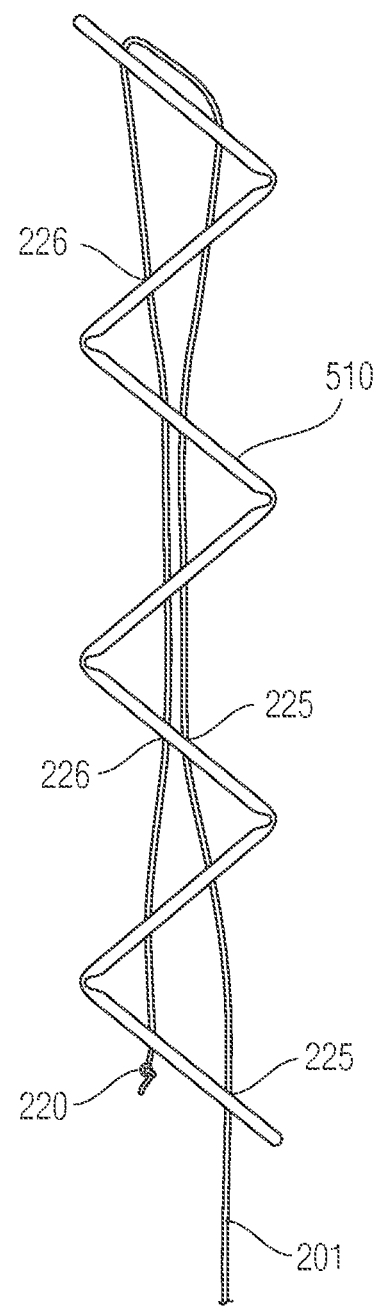

FIGS. 14a and 14b illustrate an exemplary elongated profile of an exemplary tissue anchor 500 that includes an elongated strip 510, All openings 225, 226 in both sets of the openings are aligned with each other forming a straight line parallel to the longitudinal axis of the strip 510. FIG. 14b is a side elevation view of the strip 510 showing the routing of the tensioning member 201 through the strip 510.

In various embodiments, at least one pre-set folding line is created between two pairs of the openings 225, 226, as illustrated in FIG. 11a. The pre-set folding line can be made by heat setting with or without a mold. One skilled in the art would understand that other methods can also be used to create pre-set folding lines without undue experimentations. In some embodiments, the pre-set folding lines allow the elongated strip to fold at pre-defined places. In certain embodiments, a pre-set folding line is created between every two pairs of the openings 225, 226, for example, as illustrated in FIGS. 12-14.

Figure 15:
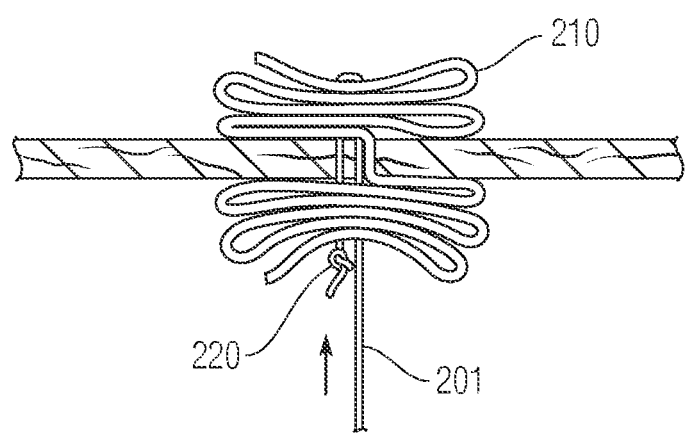
FIG. 15 is a perspective view of an exemplary tissue anchor deployed across a tissue in accordance with the present teachings.

According to various embodiments of the present teachings, the elongated strip (e.g., strip 210) shortens and creates folds as illustrated in FIG. 15. In some embodiments, the number of the folds in the tissue anchor in its deployed profile ranges from 4 to 12. In various embodiments, the number of the folds is the same as the number of the openings in at least one set of the openings 225, 226. In other embodiments, the number of the folds has no particular relationship with the number of the openings in either set of the openings 225, 226. In various embodiments, the number of the folds is the same as the number of the pre-set folding lines plus one. In other embodiments, the number of the folds has no particular relationship with the number of the pre-set folding lines. In various embodiments, upon deployment, at least half number of the folds is distal to the treatment tissue and the rest of the folds are proximal to the treatment tissue. In other embodiments, upon deployment, less than half of the folds are distal to the treatment tissue and the rest of the folds are proximal to the treatment tissue. In yet other embodiments, upon deployment, more than half of the folds are distal to the treatment tissue and the rest of the folds are proximal to the treatment tissue.

In various embodiments, the tensioning member extends through the openings along the elongated strip such that tightening the tensioning member will cause the elongated strip to fold. Although certain examples of tissue anchor deployment are described herein, one with ordinary skill in the art would appreciate that deployment of the tissue anchor may take on various forms due to the flexible nature of the strip, especially when a highly flexible fabric or other materials is used. For example, a fabric material or other similarly flexible materials may be folded or otherwise deformed during a deployment to a tissue site.

Figure 16A:
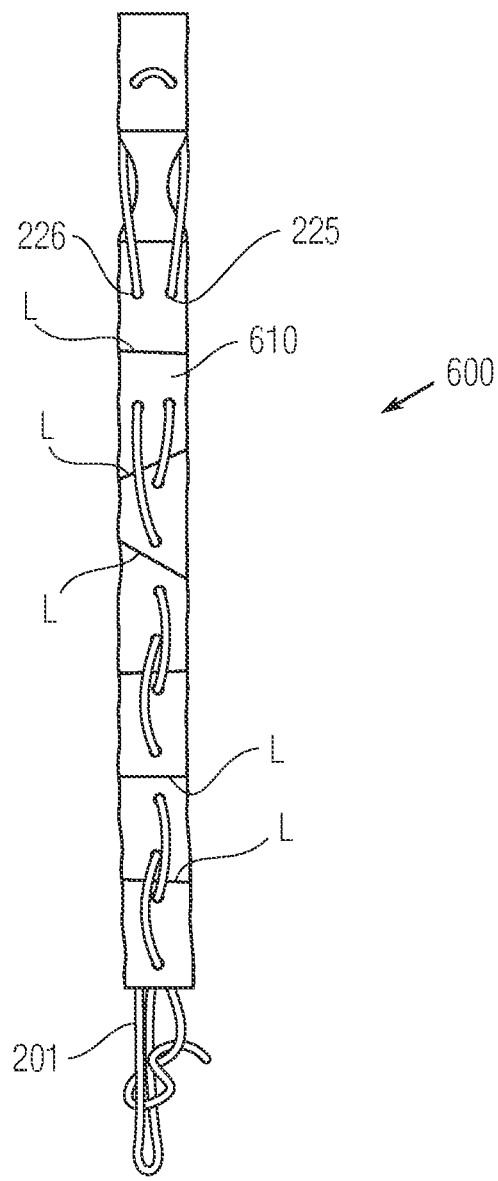
FIG. 16a is a perspective view of an exemplary tissue anchor in accordance with the present teachings.
Figure 16B:
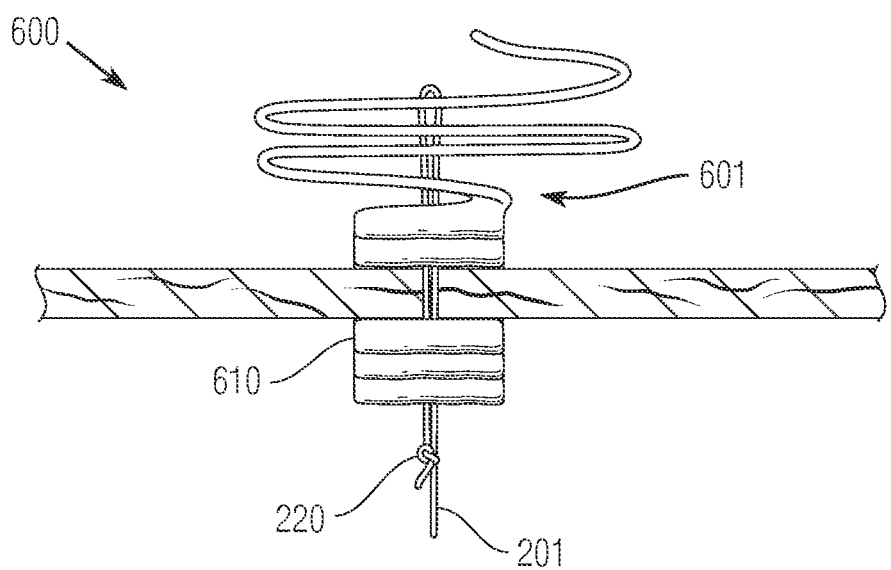
FIG. 16b is a cross-sectional view of an exemplary tissue anchor deployed across a tissue in accordance with the present teachings.

FIGS. 16a-d illustrate an exemplary embodiment of the present teachings. Specifically, FIGS. 16a and 16b illustrate an exemplary elongated profile and an exemplary deployed profile, respectively, of a tissue anchor 600 of the present teaching. The tissue anchor 600 includes an elongated strip 610. As shown in FIG. 16a, the elongated strip 610 has two sets of openings 225, 226 through which the tensioning member 201 weaves. The tensioning member 201 weaves through the first set of openings 225 as it extends from the proximal end to the distal end of the strip 610 and weaves through the second set of openings 226 as it returns from the distal end to the proximal end of the strip 610.

In various embodiments of the present teachings, at least one opening in the first set of openings corresponds with another opening in the second set of openings and together they form a pair of openings on the strip. As shown in FIG. 16a, there are 5 pairs of openings 225, 226 in the distal portion of the strip, and 3 pairs of openings 225, 226 in the proximal portion of the strip 510. As shown in FIG. 16a, each pair of the openings 225, 226 in the distal end section of the distal portion of the strip form an imaginary line and the imaginary lines from the opening pairs 225, 226 in the distal portion of the strip 610 are parallel to one another and perpendicular to the longitudinal axis of the strip 610, and at the lateral center of the strip 610; all openings 225, 226 in the proximal end section of the distal portion of the strip 610 align with one another and form an imaginary straight line that is parallel to the longitudinal axis of the entire distal portion of the strip 610, and at the lateral center of the entire distal portion of the strip 610. Thus, in the proximal portion of the strip 610, all openings 225, 226 from both set of openings align with one another and form an imaginary straight line that is parallel to the longitudinal axis of the strip 610 and at the lateral center of the strip 610. One skilled in the art should understand that the amount of pairs of opening in distal and/or proximal portion of the strip 610 can be of any number other than what has been described here.

FIG. 16a further illustrates exemplary pre-set folding lines in an elongate strip of the present teachings. As shown in FIG. 16a, the folding lines (indicated in the drawings as "L") in the proximal portions and the distal end portion of the distal portion of the strip 610 are parallel to one another and perpendicular to the longitudinal axis of the strip 610. The pre-set folding lines L between the distal end section and proximal end section of the distal portion of the strip 610 are angled to the other pre-set folding lines L. Although specific pre-set folding patterns is shown in FIG. 16a, one with ordinary skill in the art would understand that other patterns, numbers can be incorporated to form pre-set folding lines L. For example, the both distal and proximal portions of the strip 610 are parallel to one another and perpendicular to the longitudinal axis of the strip 610, and only a middle portion 615 between the distal and proximal portions of the strip 610 are angled, so as to forming a transitional section across the tissue upon deployment. Therefore what is shown in FIG. 16a should not be considered as being limiting.

FIG. 16a further illustrates an exemplary narrow section in the distal end portion of the strip. This narrow section is the result of radiopaque marker being crimped onto the strip. As described above, there are other ways of putting one or more radiopaque markers onto the strip. Thus, what is shown in this Figure should not limit the scope of the present teachings.

FIG. 16b illustrates an exemplary deployment profile of an embodiment of the present teachings across a treatment tissue. There are 8 folds in the deployed tissue anchor as shown in FIG. 16b, among which 5 are distal to the tissue and 3 are proximal to the tissue. One skilled in the art would understand that the number of folds in each side of the tissue should not be viewed as limiting. As shown in FIG. 16b, the folded panels at the proximal portion of the strip and at the proximal end section of the distal portion of the strip orientate in one direction, and the folded panels in the distal end portion of the strip orientate in another direction that is perpendicular to folded panels in the other direction. The transitional folds between the distal and proximal end section of the distal portion of the strip are located at the angled pre-set folding line. In this specific embodiment shown in FIG. 16b, the transitional folds are distal to the tissue and are generally indicated with the reference character 601 (in other words, the change in folding direction is identified at 601). One skilled in the art should understand that the transitional folds can be proximal to the tissue, or across the tissue, and thus what has be illustrated here should not be viewed as limiting.

Figure 16C:
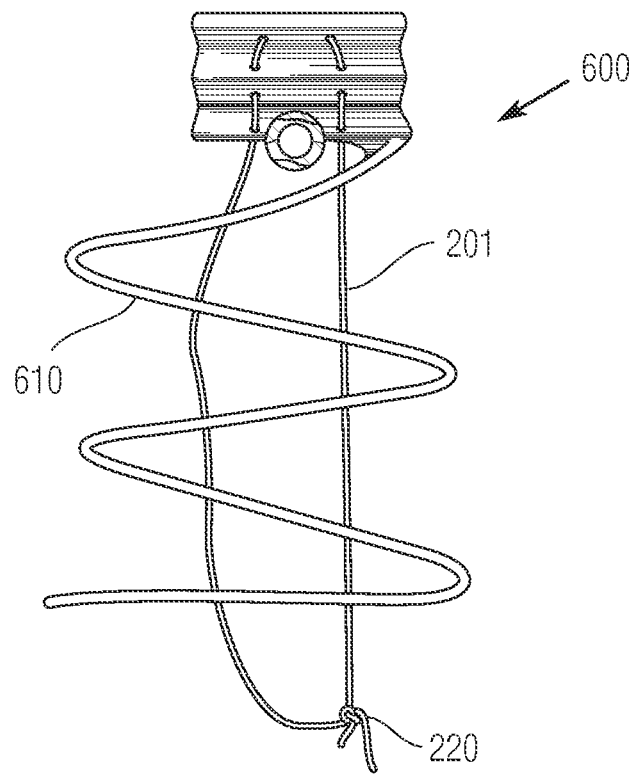
FIG. 16c is a side elevation view of the tissue anchor of FIGS. 16a-b.

FIG. 16c is a view of the exemplary tissue anchor shown in FIGS. 16a-b in its deployed configuration. The distal deployed anchor portion has a width "x" established by the width of the tissue anchor and a length "y" determined by the distance between two pairs of the openings. The proximal deployed anchor portion has a width "y" established by the distance between the two pairs of the openings and a length "x" established by the width of the tissue anchor. As shown in this view, the configuration in the exemplary embodiment shown in FIGS. 16a-d increases the overall width of the deployed anchor. This configuration prevents the tensioning member from cutting the panel and the tissue and increases the retention force of the tissue anchor against the tissue.

Figure 16D:
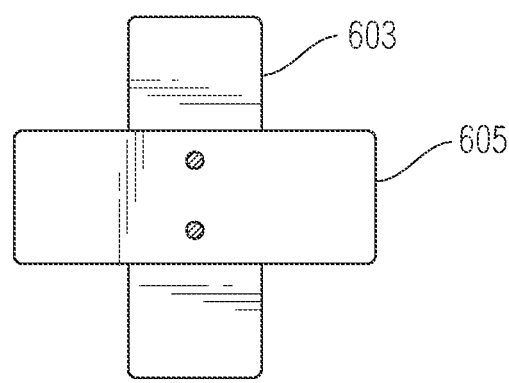
FIG. 16d is top plan view of the tissue anchor of FIGS. 16a-b.

In other words as shown in FIG. 16d, at least two adjacent anchor panels 603, 605 are disposed in a crisscrossed manner in that the longitudinal axes of the adjacent anchor panels 603, 605 are disposed perpendicular to one another as shown.

Other arrangements can be incorporated into the two sets of openings. For example, all the openings from both sets of openings in the distal portion of the strip can align with each other to form an imaginary straight line that is parallel to the longitudinal axis of the strip, and/or each pair of the openings in the proximal portion of the strip can form an imaginary line and all the imaginary lines so formed are parallel to one another and perpendicular to the longitudinal axis of the strip. One skilled in the art would understand that openings in either or both set of the openings can form any configuration so long as it serves the intended purpose.

Figure 17A:
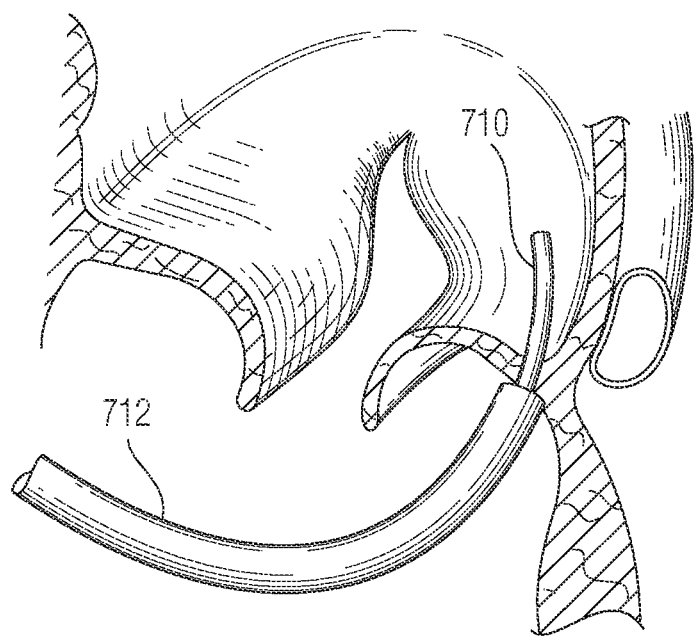
FIG. 17a is a perspective view of an exemplary tissue anchor deploying across a tissue in accordance with the present teachings.
Figure 17B:
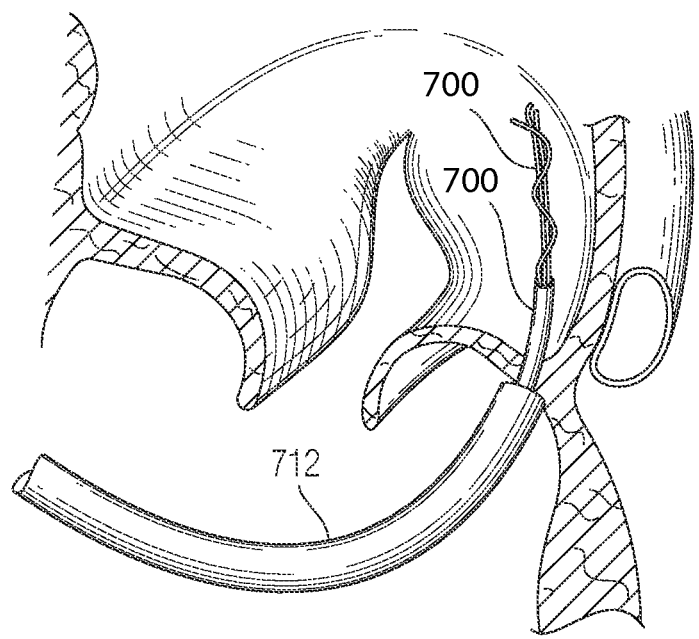
FIG. 17b is a perspective view of an exemplary tissue anchor deploying across a tissue in accordance with the present teachings.
Figure 17C:
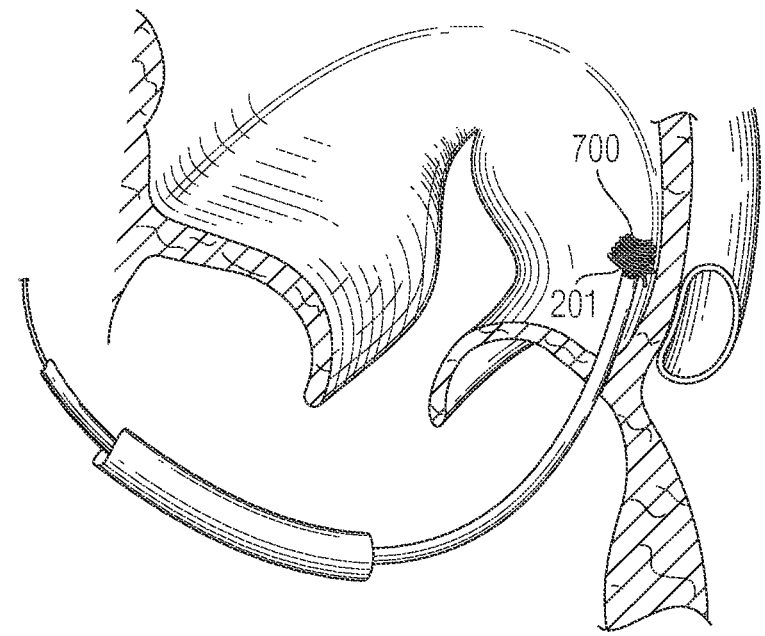
FIG. 17c is a perspective view of an exemplary tissue anchor deploying across a tissue in, accordance with the present teachings.
Figure 17D:
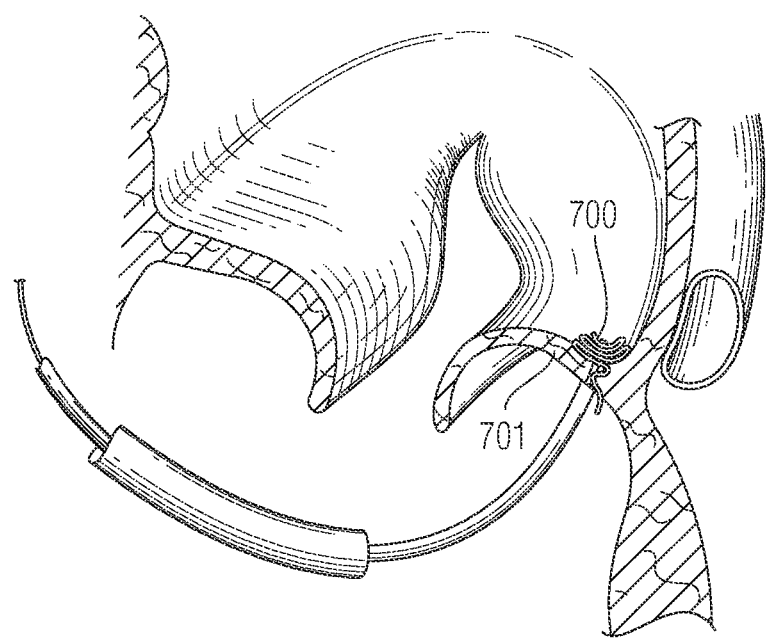
FIG. 17d is a perspective view of an exemplary tissue anchor deploying across a tissue in accordance with the present teachings.
Figure 17E:
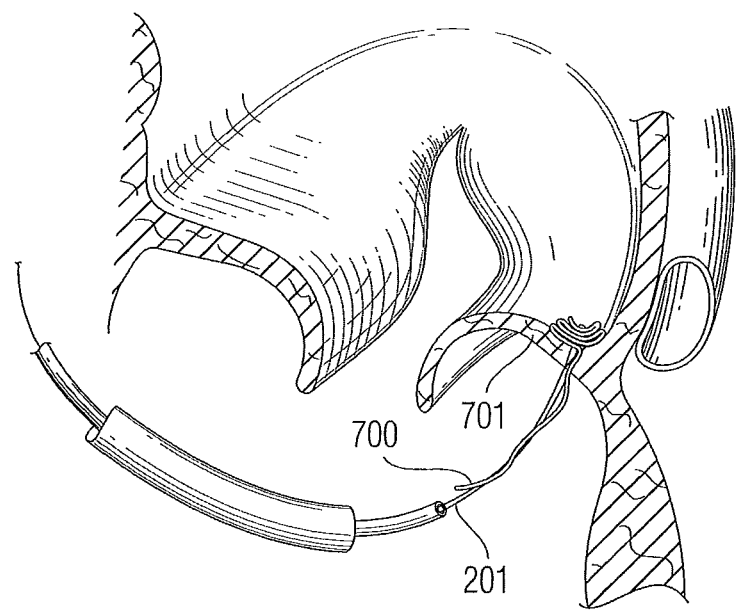
FIG. 17e is a perspective view of an exemplary tissue anchor deploying across a tissue in accordance with the present teachings.
Figure 17F:
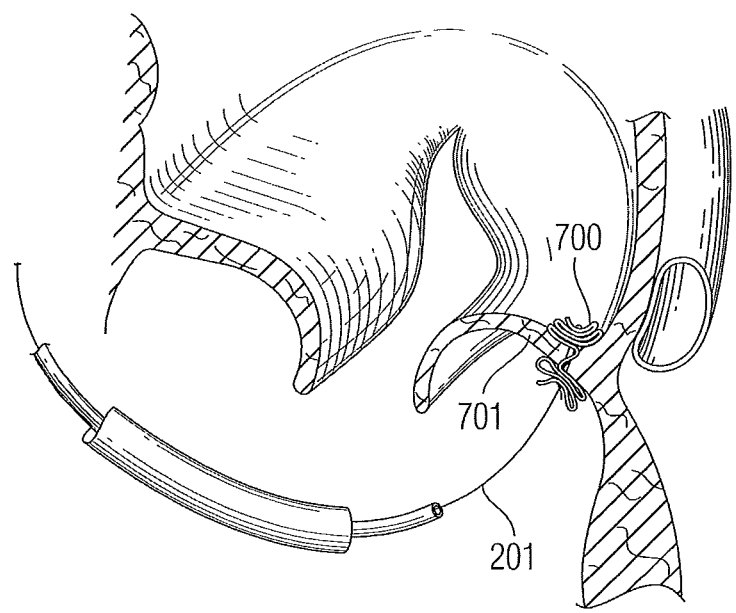
FIG. 17f is a perspective view of an exemplary tissue anchor deploying across a tissue in accordance with the present teachings.

FIGS. 17a-f illustrate an exemplary deployment of a tissue anchor 700 of the present teachings across a tissue 701. It will be understood that tissue anchor 700 can be in the form of any of the tissue anchors disclosed herein and is numbered herein as 700 only out of convenience. As illustrated in FIG. 17a, a delivery catheter 710, which can be contained within an outer catheter 712, carries the tissue anchor 700 in its elongated profile across an aperture in the tissue 701. In some embodiments of the present teachings, as illustrated in FIG. 17b, the delivery catheter 710 is withdrawn proximally to expose the distal portion of the elongated tissue anchor 700. Alternatively, the elongated tissue anchor 700 is pushed proximally outside of the delivery catheter 710. FIG. 17c shows the deployment of the distal portion of the tissue anchor 700. In one embodiment, the free end of the tensioning member 201 is pulled proximally to shorten the longitudinal length of the distal portion of the tissue anchor 700, such as by creating folds. FIG. 17d shows the delivery catheter 710 holding the elongated proximal portion of the tissue anchor 700 is further pulled proximally, causing the deployed distal portion of the tissue anchor 700 seat firmly against the distal side of the tissue 701. As shown in FIG. 17e, the delivery catheter 710 is further pulled proximally, exposing the proximal portion of the tissue anchor 700. As further shown in FIG. 17f, the proximal portion of the tissue anchor 700 is deployed by pulling the free end of the tensioning member 201 proximally, which draws the proximal portion of an elongated strip 705 toward the proximal side of the tissue 701. After the distal portion of the tissue anchor 700 securely compress the tissue 701 at the distal side, and the proximal portion of the tissue anchor 700 securely compress the tissue 701 at the proximal side, a locking member can be used to secure the tensioning member 201 in its tensioned state so that the distal and proximal portions of the tissue anchor 700 remain compressed against the tissue 701.

Certain specific details are set forth in the following description and Figures to provide an understanding of various embodiments of the present teachings. Those of ordinary skill in the relevant art will understand that various features of the teaching may be used alone or in numerous combinations depending on the needs and preferences of the user. Those skilled in the art can also practice other embodiments of the present teachings without one or more of the details described below. Thus, it is not the intention of the Applicants to restrict or in any way limit the scope of the appended claims to such details. While various processes are described with reference to steps and sequences in the following disclosure, the steps and sequences of steps should not be taken as required to practice all embodiments of the present teachings.

As used herein, the term "proximal" means closest to the operator (less into the body) and "distal" means furthest from the operator (further into the body). In positioning a medical device from a downstream access point, distal is more upstream and proximal is more downstream.

As used herein, the term "tensioning member" means a member which can take forms of a suture, cable, wire or any other small diameter, flexible, semi-rigid or rigid material having a suitable tensile strength for the intended use. In addition, as used herein, the term "wire" can be a strand, a cord, a fiber, a yarn, a filament, a cable, a thread, or the like, and these terms may be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

What is claimed is:

1. A tissue anchor comprising:
    a generally flexible elongate continuous anchor member capable of being inserted through tissue and moving between an elongate configuration and a shortened configuration suitable for anchoring against at least one side of the tissue, the anchor member having a proximal end portion and a distal end portion, wherein the anchor member has a first set of openings and a second set of openings formed therein at spaced locations along a length of the anchor member; and
    a tensioning member operatively connected to the anchor member such that the anchor member can slide relative to the tensioning member, the tensioning member extending through the proximal end portion to the distal end portion by passing through the first set of openings and then back to an anchor point at the proximal end portion by passing through the second set of openings, the tensioning member capable of causing the anchor member to transform from the elongate configuration to the shortened configuration, wherein the anchor member can compress along a length thereof and thereby adjust to a thickness of the tissue; wherein the anchor member is configured to form a plurality of folded panels upon pulling the tensioning member, and
    wherein, in the shortened configuration, the plurality of folded panels consists of a set of first panels that are oriented in a first direction and a set of second panels that are oriented in a second direction that is perpendicular to the folded set of first panels.

2. The tissue anchor of claim 1, wherein the first panels are located in the proximal end portion and at least partially within the distal end portion and the set of second panels are located within the distal end portion.

3. The tissue anchor of claim 1, wherein the anchor member includes at least one first transitional fold line formed within the distal end portion and a plurality of second fold lines formed both within the proximal and distal end portions, the second fold lines having a different orientation than the at least one first transitional fold line to cause the anchor member to have a change in a folding direction along the distal end portion and relative to folding of an adjacent section of the distal end portion and the proximal end portion upon pulling the tensioning member.

4. The tissue anchor of claim 3, wherein the at least one first transitional fold line comprises a plurality of first transitional fold lines located between distal and proximal end sections of the distal end portion.

5. The tissue anchor of claim 4, wherein the second fold lines are parallel to one another and are formed perpendicular to a longitudinal axis of the anchor member, while the first transitional fold lines are formed non-parallel to the second fold lines and at an angle other than 90 degrees relative to the longitudinal axis.

6. The tissue anchor of claim 4, wherein adjacent first transitional fold lines are formed non-parallel to one another.

7. The tissue anchor of claim 1, wherein in the distal end portion, at least some openings belonging to the first and second sets of openings define pairs of openings each pair defined by one first opening and one second opening, each pair of openings defined by a line that passes through the one first opening and one second opening, wherein the lines of the associated pairs of openings are parallel to one another and are perpendicular to a longitudinal axis of the anchor member.

8. The tissue anchor of claim 7, Wherein all of the openings formed in the proximal end portion are aligned with one another along a line that is parallel to the longitudinal axis of the anchor member.

9. The tissue anchor of claim 8, Wherein all of the openings formed in the proximal end portion are formed at a lateral center of the anchor member.

10. The tissue anchor of claim 1, wherein the distal end portion includes a narrow section spaced from a distal end of the anchor member and of reduced width caused by a radiopaque marker that is crimped about the anchor member.

11. The tissue anchor of claim 1, wherein the generally flexible elongate anchor member is formed from a material selected from at least one of: natural fibers, synthetic fibers, polymers and metals.

12. The tissue anchor of claim 1, wherein the tensioning member comprises a suture.

13. The tissue anchor of claim 1, wherein the tensioning member includes a stop member engageable with the anchor member.

14. The tissue anchor of claim 13, wherein the stop comprises a knot in the tensioning member.

15. A tissue anchor comprising:
    a generally flexible elongate continuous anchor member capable of being inserted through tissue and moving between an elongate configuration and a shortened configuration suitable for anchoring against at least one side of the tissue, the anchor member having a proximal end portion and a distal end portion, wherein the anchor member has a set of first openings and a set of second openings formed therein at spaced locations along a length of the anchor member; and
    a tensioning member operatively connected to the anchor member such that the anchor member can slide relative to the tensioning member, the tensioning member extending through the proximal end portion to the distal end portion by passing through the first set of openings and then back to an anchor point at the proximal end portion by passing through the second set of openings, the tensioning member capable of causing the anchor member to transform from the elongate configuration to the shortened configuration, wherein the anchor member can compress along a length thereof and thereby adjust to a thickness of the tissue; wherein the anchor member is configured to form a plurality of folded panels upon pulling the tensioning member, and wherein, in the shortened configuration, the plurality of folded panels consists of a set of first panels that are oriented in a first direction and a set of second panels that are oriented in a second direction that is perpendicular to the folded set of first panels, wherein each second panel includes one first opening and one second opening through which the tensioning member passes.

* * * * *